United States Patent
Gray et al.

(10) Patent No.: US 11,684,579 B2
(45) Date of Patent: Jun. 27, 2023

(54) MULTI-VESICULAR LIPOSOMES FOR TARGETED DELIVERY OF DRUGS AND BIOLOGICS FOR TISSUE ENGINEERING

(71) Applicant: KARMA BIOTECHNOLOGIES, Los Angeles, CA (US)

(72) Inventors: Andrew Brovko Gray, Los Angeles, CA (US); Donald Dewane Johnson, Fontana, CA (US); Alan Michael Johnson, Monrovia, CA (US)

(73) Assignee: KARMA BIOTECHNOLOGIES, Los Angeles, CA (US)

( * ) Notice: Subject to any disclaimer, the term of this patent is extended or adjusted under 35 U.S.C. 154(b) by 172 days.

(21) Appl. No.: 17/050,556

(22) PCT Filed: Apr. 29, 2019

(86) PCT No.: PCT/US2019/029628
§ 371 (c)(1),
(2) Date: Oct. 26, 2020

(87) PCT Pub. No.: WO2019/210296
PCT Pub. Date: Oct. 31, 2019

(65) Prior Publication Data
US 2021/0186878 A1    Jun. 24, 2021

Related U.S. Application Data

(60) Provisional application No. 62/663,623, filed on Apr. 27, 2018.

(51) Int. Cl.
*A61K 9/127* (2006.01)
*A61K 9/51* (2006.01)
(Continued)

(52) U.S. Cl.
CPC .......... *A61K 9/1277* (2013.01); *A61K 9/5123* (2013.01); *A61K 45/06* (2013.01); *B82Y 5/00* (2013.01)

(58) Field of Classification Search
CPC .... A61K 9/1277; A61K 9/5123; A61K 45/06; A61K 31/337; A61K 9/127; B82Y 5/00; C07K 16/00
See application file for complete search history.

(56) References Cited

U.S. PATENT DOCUMENTS 5,993,851 A    11/1999  Foldvari
10,517,823 B1 * 12/2019  Kam ................. A61K 39/395
(Continued)

FOREIGN PATENT DOCUMENTS

EP    2889039 A1    7/2015
WO   98/14171 A1    4/1998
(Continued)

OTHER PUBLICATIONS

Kisak, E.T., et al Current Medicinal Chemistry, vol. 11, pp. 199-219, 2004.*
(Continued)

*Primary Examiner* — Gollamudi S Kishore
(74) *Attorney, Agent, or Firm* — Brooks Kushman P.C.

(57) ABSTRACT

A multivesicular liposome composition includes a plurality of multivesicular liposomes. Each multivesicular liposome includes a carrier liposome particle including carrier phospholipid bilayer and having an average diameter less than 1 micron; and at least one sub-chamber liposome nanoparticle including a sub-chamber liposome nanoparticle bilayer and having an average diameter less than about 50 nm. The carrier liposome particle encapsulates the at least one sub-chamber liposome nanoparticle. Characteristically, tail groups of the carrier liposome phospholipids are larger than (Continued)

tail groups phospholipids of the at least one sub-chamber liposome nanoparticle.

26 Claims, 15 Drawing Sheets

(51) Int. Cl.
*A61K 45/06* (2006.01)
*B82Y 5/00* (2011.01)

(56) References Cited

U.S. PATENT DOCUMENTS

| | | | | |
|---|---|---|---|---|
| 2002/0061331 | A1* | 5/2002 | Zasadzinski | A61K 9/1274 514/18.1 |
| 2004/0073295 | A1* | 4/2004 | Chaikof | C07F 9/10 623/1.46 |
| 2011/0105995 | A1 | 5/2011 | Zhu et al. | |
| 2015/0196663 | A1* | 7/2015 | Shusta | A61K 9/0085 435/254.11 |

FOREIGN PATENT DOCUMENTS

| | | |
|---|---|---|
| WO | 2014/197500 A1 | 12/2014 |
| WO | 2015/126502 A2 | 8/2015 |
| WO | 2016/040940 A1 | 3/2016 |
| WO | 2016/149625 A1 | 9/2016 |

OTHER PUBLICATIONS

Dong, et al., "Packing and mobility of hydrocarbon chains in phospholipid lyotropic liquid crystalline lamellar phases and liposomes: characterization by positron annihilation lifetime spectroscopy", Physical Chemistry Chemical Physics, vol. 17, No. 1 (2015), pp. 276-286.

Somiya, et al., "One-step scalable preparation method for non-cationic liposomes with high siRNA content," In'tl J. of Pharmaceutics 490 (2015), pp. 316-323.

Werlein, et al., "Interference of phosphatidylcholines with in-vitro cell proliferation—no flock without black sheep," Biochimica et Biophysica Acta 1848 (2015), pp. 1599-1608.

European Search Report for EP Application No. 19793511.7, dated Feb. 28, 2022, 12 pages.

Grimaldi, N. et al., "Lipid-based nanovesicles for nanomedicine," Chem. Soc. Rev., 2016, 45, pp. 6520-6545.

Malam, Y. et al., "Liposomes and nanoparticles: nanosized vehicles for drug delivery in cancer," Trends in Pharmacological Sciences, v. 30, n. 11, 2009, pp. 592-599.

Zhai, Y. et al., "Advances in lipid-based colloid systems as drug carrier for topic delivery," J. of Controlled Release, 2014, v. 193, pp. 90-99.

Notification of Transmittal of the International Search Report and the Written Opinion of the International Searching Authority dated Aug. 30, 2019 for PCT Appn. No. PCT/US2019/029628 filed Apr. 29, 2019, 13 pgs.

\* cited by examiner

14:1 (Δ9-Cis) PC

14:0 PG reative olefin
16:0-16:0 (acrylate) PC

16:0 PEG-350 PE

14:1 (Δ9-Cis) PC "phospholipid"  Shape of phospholipid structure  Packing of phospholipids based on tail length

| Lane | SAMPLE ID | AMOUNT DATA |
|---|---|---|
| 1 | 1kb DNA size ladder | N/A |
| 2 | Untreated cells | 0 ng |
| 3 | Naked DNA | 0 ng |
| 4 | 1.5 µl GeneJet | 0 ng |
| 5 | 1.5 µl GeneJet | 250 ng |
| 6 | 3.0 µl GeneJet | 250 ng |
| 7 | CLSTER[DNA] | 250 ng |
| 8 | Non-crosslinked CLSTER[DNA] | 250 ng |
| 9 | PCR positive control | N/R |
| 10 | PCR positive control | N/R |

MULTI-VESICULAR LIPOSOMES FOR TARGETED DELIVERY OF DRUGS AND BIOLOGICS FOR TISSUE ENGINEERING

CROSS-REFERENCE TO RELATED APPLICATIONS

This application is the U.S. national phase of PCT Appln. No. PCT/US2019/029628 filed Apr. 29, 2019, which claims the benefit of U.S. provisional application Ser. No. 62/663,623 filed Apr. 27, 2018, the disclosures of which are incorporated in their entirety by reference herein.

TECHNICAL FIELD

The invention generally relates to controlled encapsulation and delivery of biomolecules that can be characterized as highly cytotoxic small molecule drugs, nucleotides, and biologics to disease state cells and tissues. In particular, this invention relates to improvements made in delivery, uptake and stimuli-responsive expression of genes for cellular reprogramming of diseased state cells and tissues.

BACKGROUND

Liposomal systems are soft material based nanoparticles and have been in use as carriers within extracellular environments as naturally occurring extracellular vesicles (EVs), or synthetically formulated vesicles from phospholipid formulations. Naturally occurring exosomes are known to encapsulate and deliver microRNA and protein to signal other cells of relative health, or oxidative stress. Recent innovations utilize liposome based carriers for delivery of cytotoxic drugs to disease state tissues and cells. Interest in the delivery of nucleotides and other gene editing tools, such as CRISPR/Cas9 have driven the inherent potential of liposome systems as biomimetic carriers, that will be naturally endocytosed by the healthy and/or disease state cell/tissue. Critically important, improvements in encapsulation, sorting and loading of vesicle-packaged biomolecules for eventual delivery are the driving factors of this innovation.

The prior art for this matter is the use of lipids organized into a liposome for delivery of small molecule drugs, nucleotides and biologics. Structurally, liposomal carriers are formed by bilayers of phospholipids. Phospholipid head groups are oriented to be exposed to the aqueous environment, making them ideal for functionalizing small molecule components to improve overall cellular uptake. Lipids are weakly held together in bilayers by Vander Waals interactions. As a result of the weakly associated lipids, dissipation of liposomes before complete circulation is a major deficiency. Known as multivesicular liposomes (MVLs), naturally occurring microvesicles (MVs) are large (>1 μm) single bilayer liposomes known to encapsulate multiple smaller vesicles (200 nm), forming non-concentric chambers. These chambers contain biomolecules, such as nucleotides, small molecules, metabolites, and proteins. Synthetically formulated MVLs have been demonstrated to encapsulate and deliver anti-cancer drugs and other small molecule chemotherapies.[1,2] Key to the prior art, release of biologically active therapeutics was controlled by the difference in salt concentration between the smaller vesicle compartments and the larger encapsulating vesicle. Other soft material based nanoparticles are polymer, peptide, and protein based materials.

SUMMARY

In at least one aspect, a multivesicular liposome composition that includes a plurality of multivesicular liposomes is provided. Each multivesicular liposome includes a carrier liposome particle including a carrier phospholipid bilayer comprising carrier phospholipids and having an average diameter less than 1 micron; and at least one sub-chamber liposome nanoparticle including a sub-chamber phospholipid bilayer comprising sub-chamber phospholipids and having an average diameter equal to or less than about 50 nm. The carrier liposome particle encapsulates at least one sub-chamber liposome nanoparticle. Characteristically, tail groups of the carrier liposome phospholipids are larger on average than tail groups of the sub-chamber phospholipids.

In another aspect a carrier liposome composition is provided. The carrier liposome composition includes a plurality of carrier liposomes particles. Each carrier liposomes particle a carrier phospholipid bilayer comprising carrier phospholipids and having an average diameter less than 1 micron.

In another aspect, a method for forming the multivesicular liposome composition set forth above is provided. The method includes a step of forming a plurality of sub-chamber liposome nanoparticles where the plurality of sub-chamber liposome nanoparticles have an average nanoparticle diameter less than about 50 nm. The plurality of sub-chamber liposome nanoparticles are formed from a sub-chamber liposome-forming composition that includes a first payload. A plurality of carrier liposome particles having an average particle diameter less than about 1 micron is then formed. The plurality of carrier liposome particles is formed from a carrier liposome-forming composition that includes the plurality of sub-chamber liposome nanoparticles such that sub-chamber liposome nanoparticles are encapsulated by carrier liposome particles.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

FIGURE and 9C hydrodynamic radius of the final cleaned-up product (the pellet after centrifugation) upon resuspension in PBS.

Figure 10A:
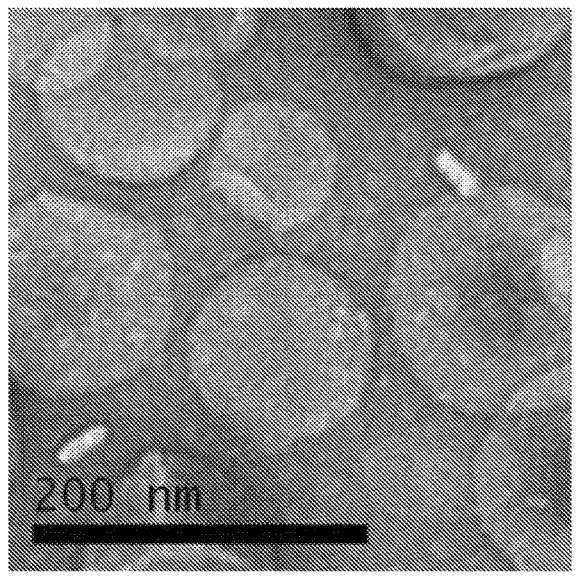
Figure 10B:
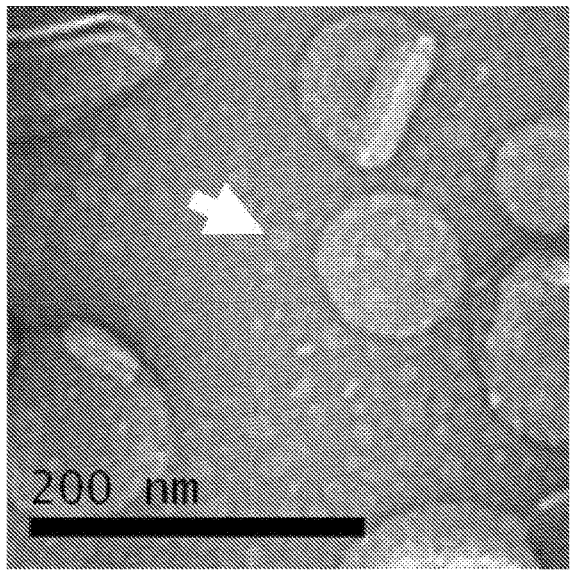
Figure 10C:
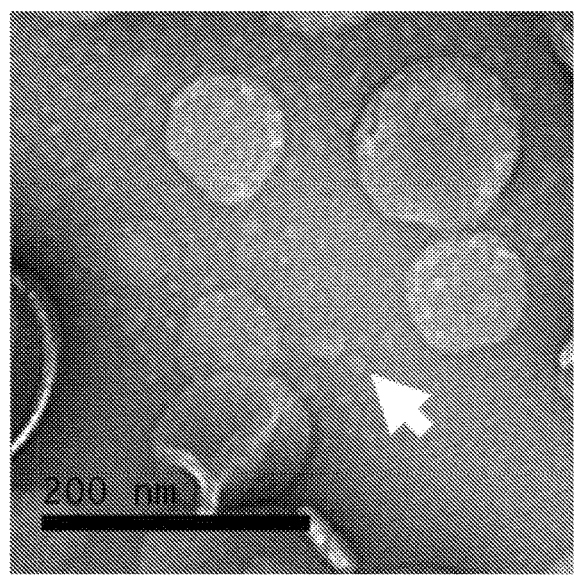

FIGS. 10A, 10B, and 10C: Visualizations of CLSTER nanoparticles and released sub-chamber nanoparticles by transmission electron microscopy.

Figures 11A, 11B:
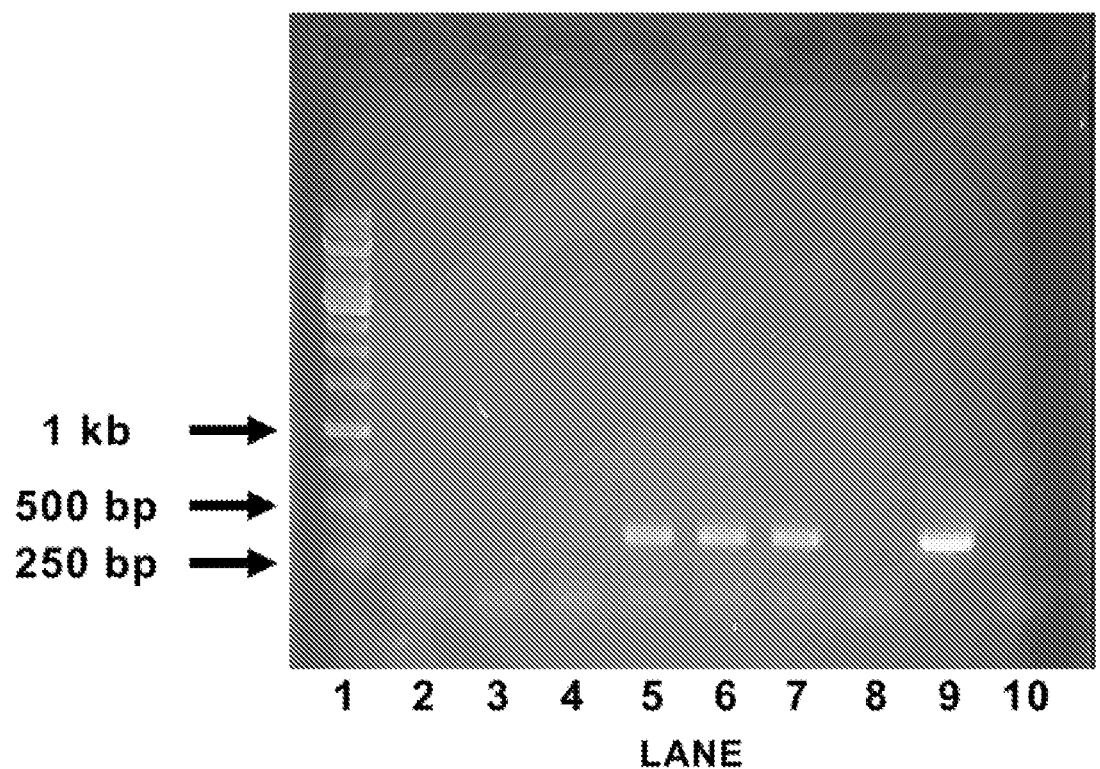

FIGS. 11A and 11B: Electrophoresis analysis for expression of mCherry mRNA by reverse-transcription PCR.

Figure 12A:
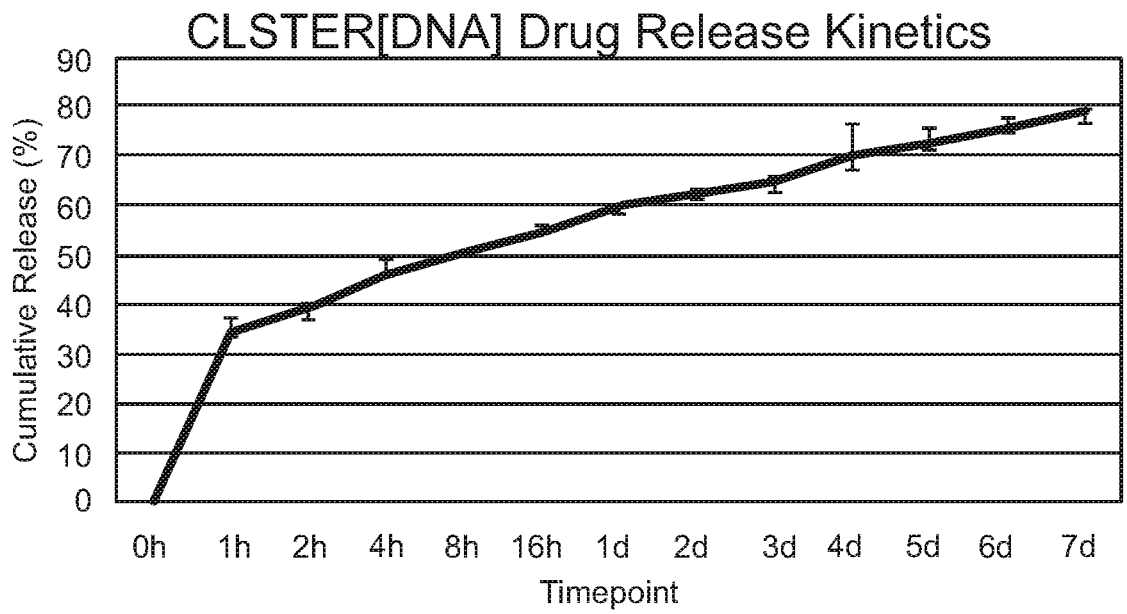
Figure 12B:
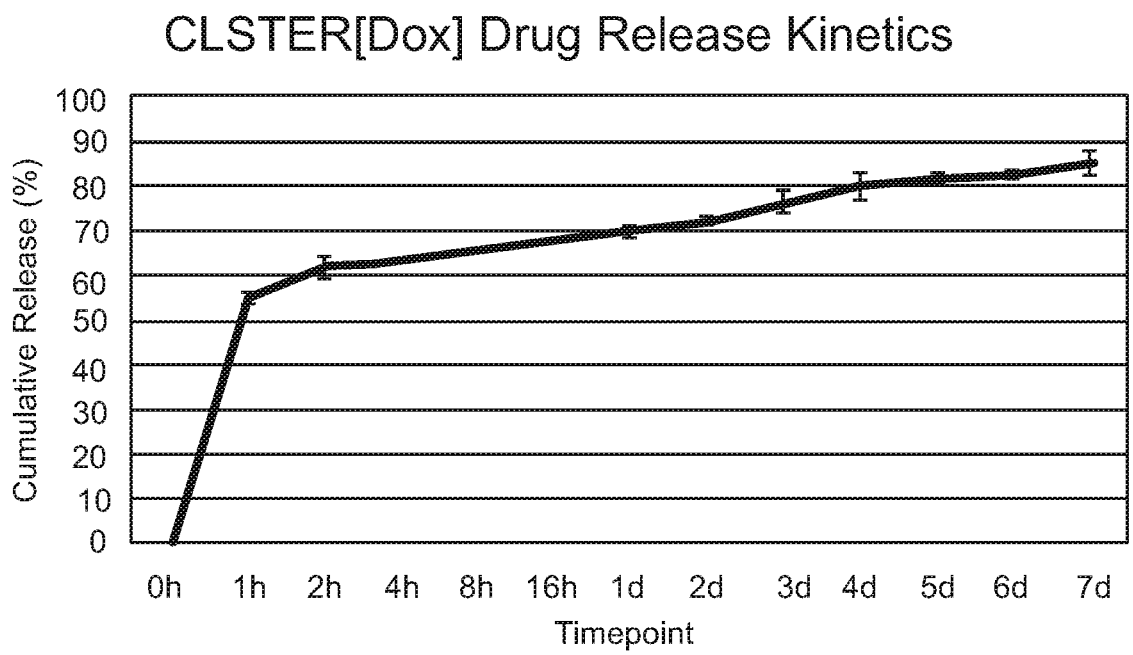
Figure 12C:
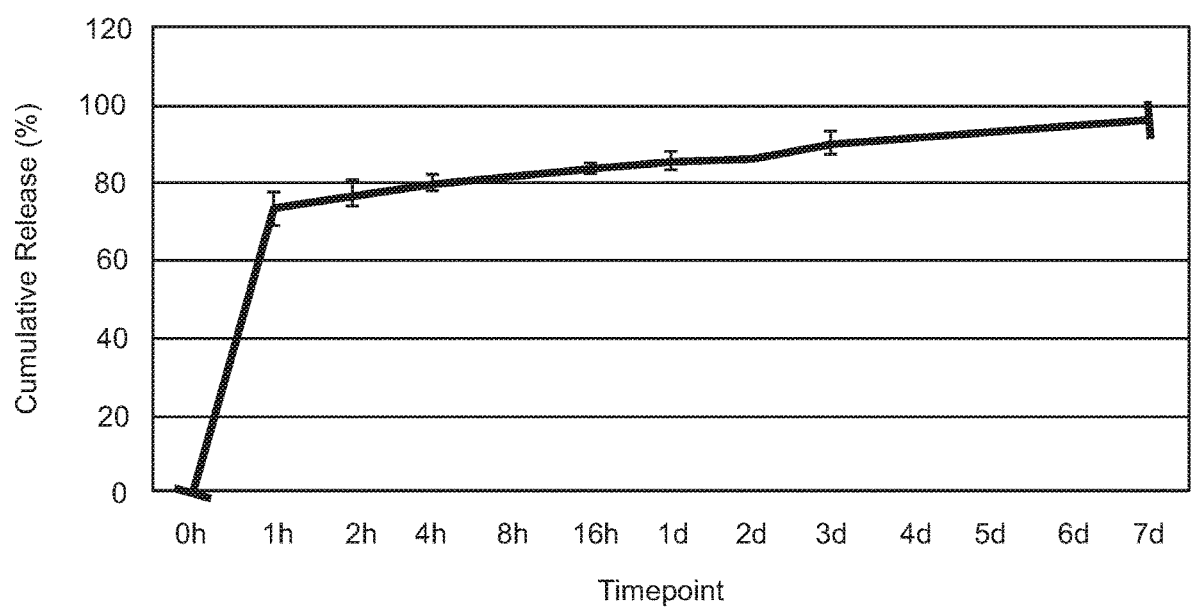

FIGS. 12A, 12B, and 12C: Plots of the release kinetics for CLSTER nanoparticles. (A) CLSTER[DNA]; (B) CLSTER [Dox]; and (C) CLSTER[BSA].

Figure 13:
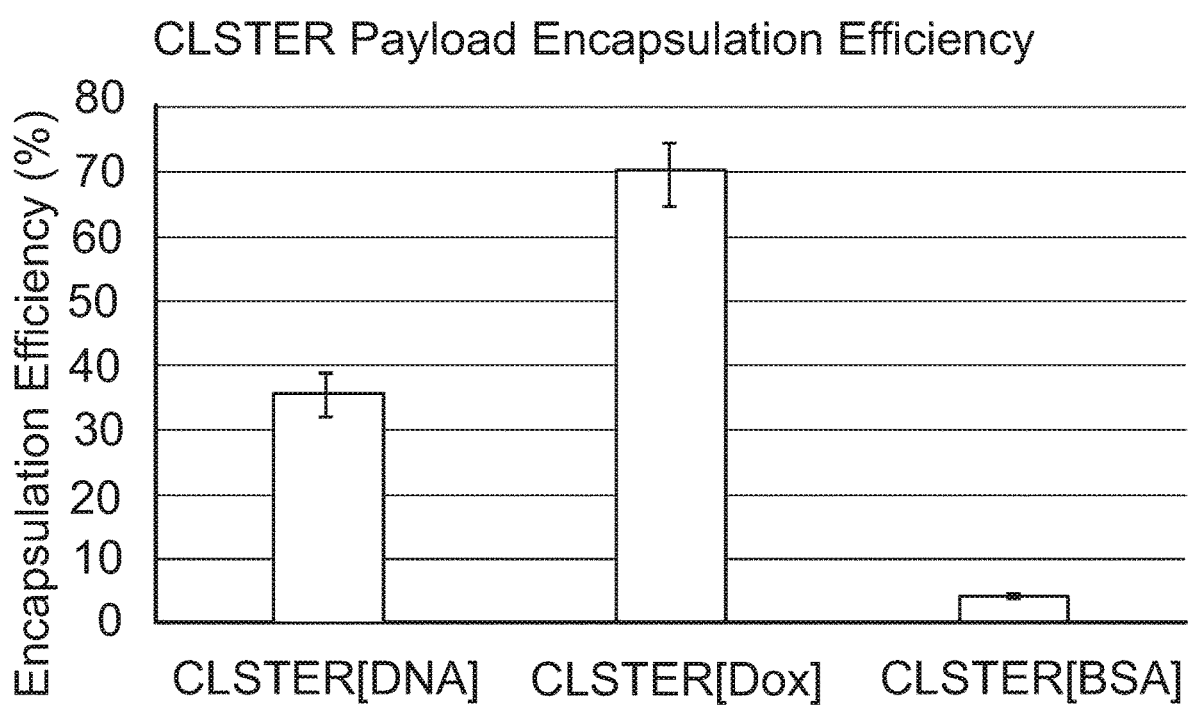

FIG. 13: Bar charts showing encapsulation efficiency of payloads in CLSTER nanoparticles.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: in the compounds herein a CH bond can be substituted with alkyl, lower alkyl, $C_{1-6}$ alkyl, $C_{6-10}$ aryl, $C_{6-10}$ heteroaryl, $-NO_2$, $-NH_2$, $-N(R'R'')_2$, $-N(R'R''R''')_3{}^+L^-$, Cl, F, Br, $-CF_3$, $-CCl_3$, $-CN$, $-SO_3H$, $-PO_3H_2$, $-COOH$, $-CO_2R'$, $-COR'$, $-CHO$, $-OH$, $-OR'$, $-O^-M^+$, $-SO3^-M^+$, $-PO3^-M^+$, $-COO^-M^+$, $-CF_2H$, $-CF_2R'$, $-CFH_3$, and $-CFR'R''$ where R', R'' and R''' are $C_{1-10}$ alkyl or $C_{6-18}$ aryl groups; single letters (e.g., "n" or "o") are 1, 2, 3, 4, or 5; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range to 100 includes 1, 2, 3, 4 . . . 97, 98, 99, 100.

Throughout this application, where publications are referenced, the disclosures of these publications in their entireties are hereby incorporated by reference into this application to more fully describe the state of the art to which this invention pertains.

Abbreviations

"CL" means cardiolipin.
"DLS" means dynamic light scattering.
"EV" means extracellular vesicle.
"MVL" means multivesicularliposome.
"PC" means phosphatidylcholine.
"pDNA" means plasmid DNA.
"PE" means phosphatidylethanolamine.
"PEG" means polyethylene glycol.
"PS" means phosphatidylserine.
"PA" means phosphatidic acid.
"PI" means phosphatidylinositol.
"PG" means phosphatidylglycerol.
"siRNA" means silencing RNAs With reference to FIG. 1, a schematic illustration of the multivesicular liposome of the invention is provided. The multivesicular liposome designed herein is referred to as "CLSTER." Multivesicular liposome 10 includes carrier liposome particle 12 and sub-chamber liposome nanoparticles 14. Carrier liposome particle 12 is a sac-like structure that encapsulates at least one sub-chamber liposome nanoparticle 14. In a refinement, carrier liposome particle 12 encapsulates a plurality of sub-chamber liposome nanoparticles 14 (e.g. 1 to 100 or 2 to 10). Carrier liposome particle 12 includes carrier phospholipid bilayer 16 that includes carrier phospholipids. Typically, carrier liposome particle 12 has a diameter (e.g., average diameter for a plurality of particles or individual particle diameter) less than 1 micron. In some refinements, carrier liposome particle 12 has a diameter (e.g., average diameter for a plurality of particles or individual particle diameter) less than, in increasing order of preference, 1 microns, 800 nm, 600 nm, 500 nm, 400 nm, or 300 nm. In a further refinement, carrier liposome particle 12 has a diameter (e.g., average diameter for a plurality of particles or individual particle diameter) greater than in increasing order of preference, 500 nm, 400 nm, 300 nm, 100 nm, 150 nm, or 200 nm. Sub-chamber liposome nanoparticle 14 includes sub-chamber phospholipid bilayer 18 that includes sub-chamber phospholipids. Typically, sub-chamber liposome nanoparticle 14 has a diameter (e.g., average diameter for a plurality of particles or individual particle diameter) equal to or less than about 50 nm. In a refinement, sub-chamber liposome nanoparticle 14 has a diameter (e.g., average diameter for a plurality of particles or individual particle diameter) from about 20 nm to about 50 nm. In a refinement, sub-chamber liposome nanoparticle has a diameter (e.g., average diameter for a plurality of particles or individual particle diameter) less than, in increasing order of preference, 80 nm, 70 nm, 60 nm, or 50 nm. In a further refinement, sub-chamber liposome nanoparticle 14 has a diameter (e.g., average diameter for a plurality of particles or individual particle diameter) greater than, in increasing order of preference, 10 nm, 15, nm, 18, nm, 20 nm, or 30 nm. Characteristically, the tail groups of the carrier phospholipids are on average larger than that the tail groups of the sub-chamber phospholipids. Multivesicular liposome 10 includes an outer surface 20 and an inner surface 22. In a refinement, polyethylene glycol groups (PEG) are attached to the outer surface 20 of multivesicular liposome 10. In some refinements, PEG groups are attached to an outer surface of sub-chamber liposome particles 14. In some refinements, reversible linkages 24 (e.g., disulfide linkage, pH sensitive linkages, electrostatic interactions, etc.) attach sub-chamber liposome nanoparticle to inner surface 22 of carrier liposome particle 12. Carrier liposome particle 12 can also encapsulate payloads 28. Similarly, sub-chamber liposome nanoparticles 14 which are also sac-like can independently encapsulate payloads 30 which can be the same or different from payloads 28. It should be appreciated that different subsets of sub-chamber liposome nanoparticles and/or subsets of the carrier liposome particles can include different payloads.

Figure 1:
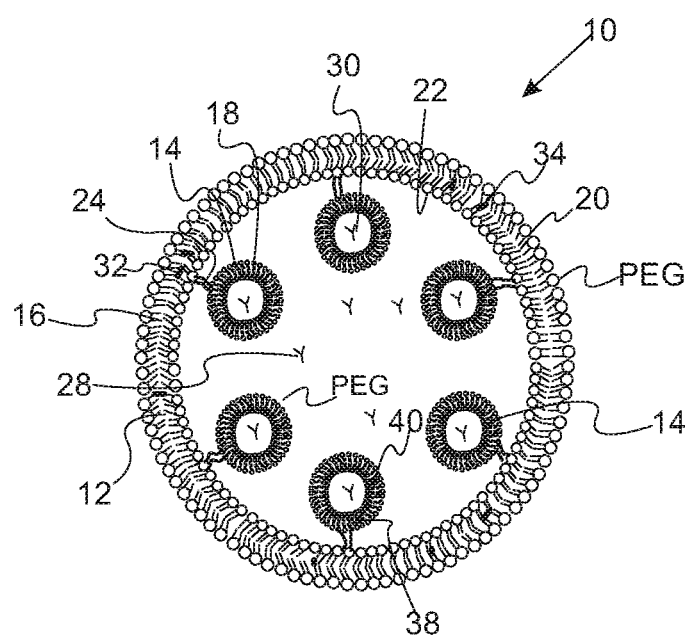
FIG. 1: Schematic of a multivesicular liposome.
Figure 2A:
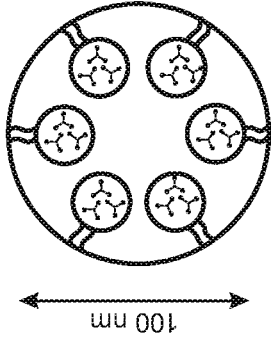
FIGS. 2A, 2B, 2C, 2D, 2E, 2F, 2G: Schematic of principle apparatus and examples of payloads. Multiple different payloads can be loaded into the sub-chamber liposome nanoparticles and/or the liposomal carrier. These payloads include, but are not limited to, one or more small molecule drugs in sub-chamber liposome nanoparticles (A), one or more polynucleotides in sub-chamber liposome nanoparticles (B), antibody in the carrier and one or more small molecule drugs in sub-chamber liposome nanoparticles (C), one or more small molecule drugs in the carrier and one or more drugs in sub-chamber liposome nanoparticles (D), different small molecule drugs in individual sub-chamber liposome nanoparticles (E), and, one or more polynucleotides and one or more small molecule drugs in individual sub-chamber liposome nanoparticles (F), and the key (G)
Figure 2B:
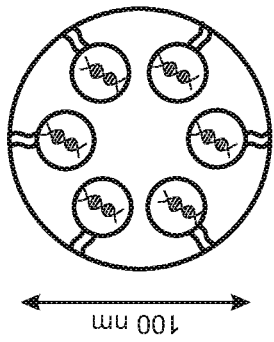
Figure 2C:
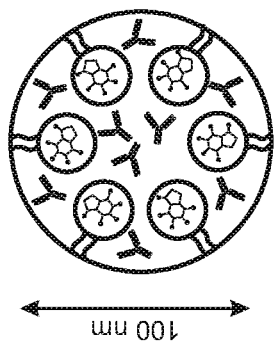
Figure 2D:
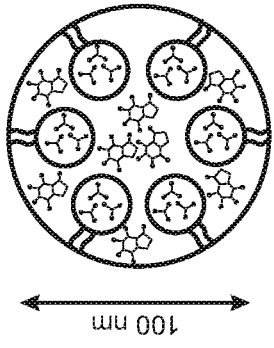
Figure 2E:
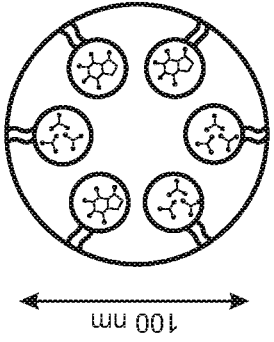
Figure 2F:
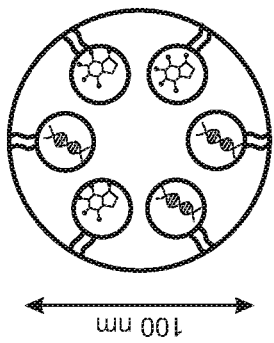
Figure 2G:
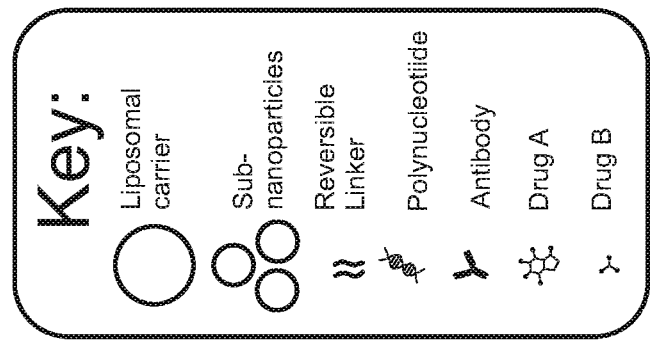

FIG. 2 illustrates a method and apparatus for delivering biomolecules (e.g. polynucleotides, small molecule drugs, or other biologics) of interest to healthy and/or disease state cells and/or tissues using the multivesicular liposome of FIG. 1. Advantageously, the multivesicular liposome provides a highly ordered, densely packed multivesicular liposome. Moreover, the multivesicular liposome includes a novel combination of seven component phospholipids (FIG. 2). Advantageously, the MVL can be used for delivery of the following therapeutic/diagnostic assets (i.e., payloads): (i) small molecule drugs, (ii) polynucleotides, such as plasmid DNA (pDNA), silencing RNAs (siRNA), messenger RNA (mRNA), (iii) and macromolecular proteins, such as fluorescent proteins, cytokines, and antibodies; and combinations thereof. The shorthand notation, CLSTER[payld] means the multivesicular liposome encapsulating a payload "payld" which can be any compound, drug, polynucleotide, or other biologic that can be delivered by the multivesicular liposome.

As set forth above, the carrier liposome particle is larger than the sub-chamber liposome nanoparticle. The size of these particles is controlled by the tail group length of the phospholipids used to make up the carrier and sub-chamber phospholipid bilayers. The following formula provides the generic structure of a phospholipid:

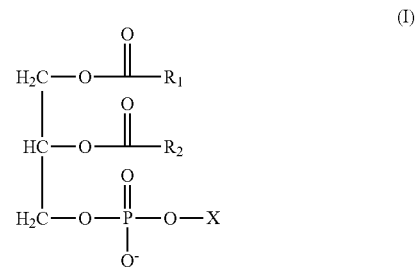

(I)

where $O=C-R_1$ and $O=C-R_2$ are tail groups; and X is the head group substituent (e.g., PC, PE, PS, PA, PI, PG or CL). In a variation, $R_1$ and $R_2$ are each independently $C_{12-20}$ alkyl (i.e., $C_{12}$, $C_{13}$, $C_{14}$, $C_{15}$, $C_{16}$, $C_{17}$, $C_{18}$, $C_{19}$, and $C_{20}$ alkyl) having 0, 1, 2, or 3 carbon-carbon double bonds. In a refinement, $R_1$ and/or $R_2$ can each independently be substituted with at least one reactive olefin group (e.g., (C=O)CHCH$_2$—an acrylate group) that assists in crosslinking. Typically, sub-chamber liposome nanoparticle phospholipids include tail groups that are smaller than the tail groups of the carrier liposome particle phospholipids. In some variations, the sub-chamber phospholipid bilayer is a combination of phospholipids having from 14 to 16 carbons (e.g., $R_1$, $R_2$ are $C_{13-15}$ alkyl with 0, 1, 2, or 3 double bonds) while the carrier phospholipid bilayer is a combination of phospholipids having from 16 to 17 carbons (e.g., $R_1$, $R_2$ are $C_{15-16}$ alkyl with 0, 1, 2, or 3 double bonds. In a variation, the sub-chamber phospholipid bilayer and the carrier phospholipid bilayer each independently 3 or 4 different phospholipids such as those described by formula I. In a refinement, the sub-chamber phospholipid bilayer and the carrier phospholipid bilayer each independently include a phospholipid with $R_1$ and/or $R_2$ having at least one double bond. In a further refinement, the sub-chamber phospholipid bilayer and the carrier phospholipid bilayer each independently include a phospholipid with $R_1$ and/or $R_2$ having at least one reactive olefin group (e.g., (C=O)CHCH$_2$— an acrylate group) as a substituent. At least some of the tail groups for sub-chamber liposome nanoparticle phospholipids and the carrier liposome particle phospholipids can include a double bond, and in particular, a cis double bond. Moreover, at least some of the tail groups for sub-chamber liposome nanoparticle phospholipids and the carrier liposome particle phospholipids can include photoactive groups that can be crosslinked when the phospholipids are included in the phospholipid bilayers. Examples of such photoactive groups include moieties with ethylenic unsaturation such as acrylate groups.

In a refinement, the smaller sub-chamber liposome nanoparticles are 20-30 nm in diameter while the larger "carrier" particle is 150-170 nm in diameter. To our knowledge, there is no prior art where a multivesicular liposome (MVL) can be formulated at smaller diameters (<1 μm), nor are there any examples where sub-chamber liposome nanoparticles, encapsulated in the carrier particle, are this small.

Chemical modifications to the head groups of phospholipids modulate charge, and/or covalently link to the carrier particle, and drive inter-bilayer association between compartments in the MVLs. This key architectural mechanism stabilizes biomolecule-encapsulated MVLs until release. The organization of the principle apparatus, in particular, the sub-chamber liposome nanoparticles are pre-formulated with encapsulated therapeutic/diagnostic assets. In addition, the ability to control the therapeutic/diagnostic assets, loaded into one (or more) different sub-chamber liposome nanoparticles, is a key novelty of our innovation.

Separate batches of pre-formulated asset-encapsulated sub-chamber liposome nanoparticles can be organized based on the encapsulating asset. For instance, assets A and B can be pre-formulated separately and combined at predetermined molar ratios in the carrier particle formulation based on the desired dose, or delivery to cell/tissue. Current manufacturing procedures and compositions of matter lack the level of control in loading particular therapeutic/diagnostic molecules at pre-determined concentrations into the sub-chamber liposome nanoparticles, followed by loading into carrier particles at pre-determined formulations. As depicted in FIG. 1, carrier liposomes 12 includes crosslinks 30 between phospholipids in the same layer bilayer and crosslinks 32 between different layers in the biolayer. Similarly, sub-chamber liposome nanoparticles 14 include crosslinks 38 between phospholipids in the same layer bilayer and crosslinks 40 between different layers in the biolayer. The organization of the principle apparatus, in particular, the bilayer composition is stabilized by a network of UV conjugated tail group covalent linkages. As a result, the liposome bilayer surface is composed of rafts of bilayers shifting based on relieving the structural strain of the particle. In nature, cells undergo this process to enhance structural stability, whereas our system is based on a series of covalent linkages between the tail groups of phospholipids. It should be appreciated that cells enhance structural stability via physical interactions between transmembrane proteins embedded within the cell's lipid bilayers, whereas the present embodiment achieves the same effect with covalent linkages between the tail groups of phospholipids.

The carrier and sub-chamber liposomes each independently include phospholipids or residues thereof. The lipids used in forming the carrier and sub-chamber bilayers are listed in Table 1. In this context the term "residues" referred to reaction products (e.g., crosslinking) of these phospholipids when such groups are included in a phospholipid bilayer.

TABLE 1

Phospholipids used in the multivesicular liposome.

| Common Name | IUPAC name | Carbon Length (tail group) | Unsaturated or saturated? | Tail group functional group |
| --- | --- | --- | --- | --- |
| 14:1 (Δ9-Cis) | 1,2-dimyristoleoyl-sn-glycero-3-phosphocholine | 14 | Unsaturated, cis- | --- |
| 14:0 PG | 1,2-dimyristoyl-sn-glycero-3-phosoph-(1'-rac-glycerol) (sodium salt) | 14 | Saturated | --- |
| 16:0-16:0 acrylate PC | 1-palmitoyl-2-[16-(acryloyloxy)palmitoyl]-sn-glycero-3-phosphorylcholine | 16 | Saturated | acrylate |
| 16:1 (Δ9-Cis) PC | 1,2-dipalmitoleoyl-sn-glycero-3-phosphocholine | 16 | Unsaturated, cis- | --- |
| 16:0 PG | 1,2-dipalmitoyl-sn-glycero-3-phospho-(1'-rac-glycerol) (sodium salt) | 16 | Saturated | --- |
| 16:0 Lysl PG | 1,2-dipalmitoyl-sn-glycero-3-[phospho-rac-(3-lysyl(1-glycerol))] (chloride salt) | 16 | Saturated | --- |
| 16:0 PEG-350 PE | 1,2-dipalmitoyl-sn-glycero-3-phosphoethanolamine-N-[methoxy(polyethylene glycol)-350] (ammonium salt) | 16 | Saturated | --- |

Figure 3:
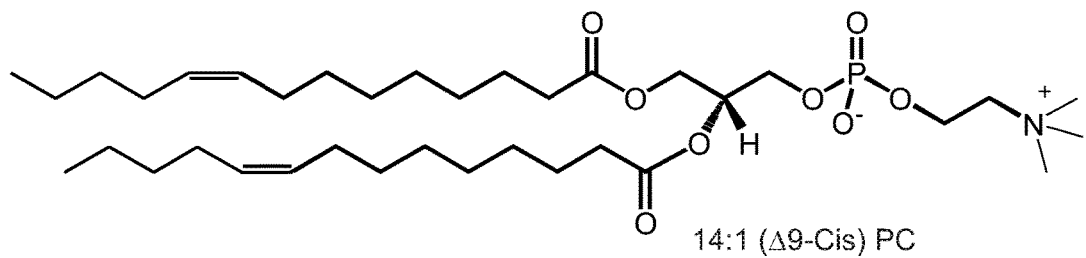
FIG. 3: Schematic of principle apparatus components (phospholipids) for sub-chamber liposome nanoparticles.
Figure 3:
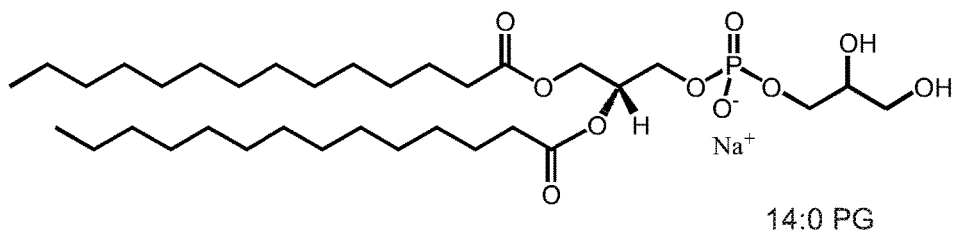
Figure 3:
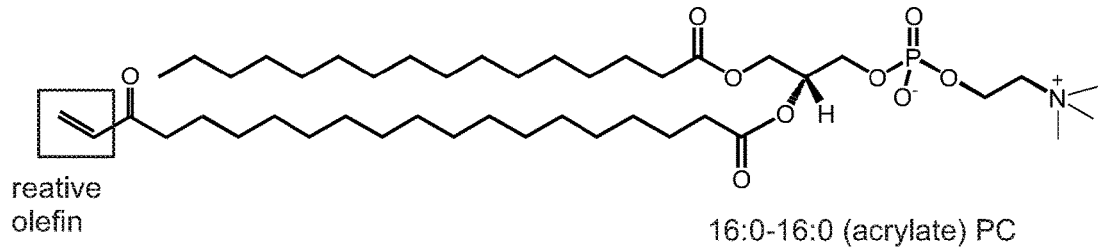
Figure 3:
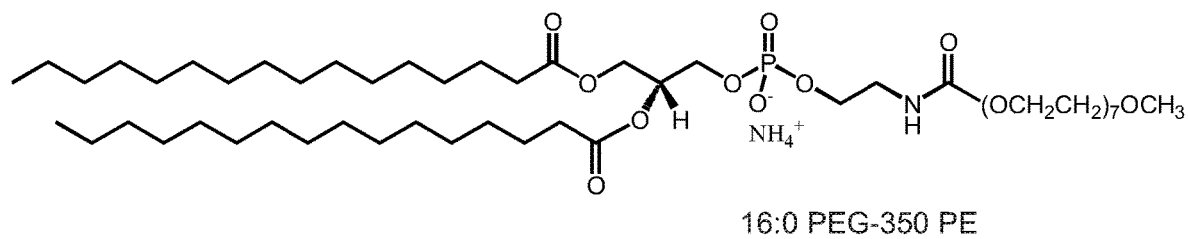

The principle apparatus of the sub-chamber liposome nanoparticles is composed of 3 or 4 unique phospholipids, organized in a molar ratio to promote a monodispersed distribution (20-30 nm in diameter) of liposomal nanoparticles. The organization of the principle apparatus, in particular, the sub-chamber liposome nanoparticles are composed of the following phospholipids: (1) 1,2-dimyristoleoyl-sn-glycero-3-posphocholine or a residue thereof; (2) 1,2-dimyristoyl-sn-glycero-3-phospho-(1'-rac-glycerol) (sodium salt) or a residue thereof; (3) 1-palmitoyl-2-[16-(acryloyloxy)palmitoyl]-sn-glycero-3-phosphorylcholine or a residue thereof, and (4) 1,2-dipalmitoyl-sn-glycero-3-phosphoethanolamine-N-[methoxy(polyethylene glycol)-350] (ammonium salt) or a residue thereof. (FIG. 3). In a variation, the 1,2-dimyristoleoyl-sn-glycero-3-phosphocholine or a residue thereof is present in 10 mole percent to 25 mole percent of the total amount of phospholipids; 1,2-dimyristoyl-sn-glycero-3-phospho-(1'-rac-glycerol)(sodium salt) or a residue thereof is present in an amount from about 30 mole percent to about 50 mole percent of the total amount of the phospholipids; 1-palmitoyl-2-[16-(acryloyloxy)palmitoyl]-sn-glycero-3-phosphorylcholine or a residue thereof is present in an amount from about 30 mole percent to about 50 mole percent of the total amount of the phospholipids; and 1,2-dipalmitoyl-sn-glycero-3-phosphoethanolamine-N-[methoxy(polyethylene glycol)-350] (ammonium salt) or a residue thereof is present in an amount from about 2 mole percent to 15 mole percent of the total amount of phospholipids.

The organization and stability of the sub-chamber liposome nanoparticle apparatus is promoted by the crosslinking of 16:0 acrylate PC phospholipid tail groups, upon formation of bilayers in an aqueous solution. The crosslinking of tail groups is driven by a photo-initiator (e.g., 2-hydroxy-4'-(2-hydroxyethoxy)-2-methlpropiophenone [HEM]), which forms a radical intermediate at carbon-16 (FIG. 3; 16:0 Acrylate PC, reactive terminal olefin) upon exposure to UV light. The radical intermediate reacts with other neighboring tail groups in a chain reaction, until there are no more reactive terminal olefins. As a result, the sub-chamber liposome nanoparticle's phospholipid bilayers are "locked" in segments that migrate along the surface of the liposome, as set forth above.

The principle apparatus of the "carrier" particle is composed of 4 unique phospholipids, organized in a molar ratio to promote a monodispersed distribution (100-200 nm in diameter) of liposomal nanoparticles. The organization of the principle apparatus, in particular, the "carrier" particle is composed of the following phospholipids: (1) 1,2-dipalmitoleoyl-sn-glycero-3-phosphocholine; (2) 1,2-dipalmitoyl-sn-glycero-3-phospho-(1'-rac-glycerol) (sodium salt); (3) 1-palmitoyl-2-[16-(acryloyloxy)palmitoyl]-sn-glycero-3-phosphorylcholine, and; (4) 1,2-dipalmitoyl-sn-glycero-3-[phospho-rac-(3-lysyl(1-glycerol))](chloride salt). In a variation, 1,2-dimyristoleoyl-sn-glycero-3-phosphocholine or residues thereof are present in an amount from 10 mole percent to 30 mole percent of the total amount of the phospholipids; 1,2-dipalmitoyl-sn-glycero-3-phospho-(1'-rac-glycerol)(sodium salt) or residues thereof are present in an amount from about 5 mole percent to about 20 mole percent of the total amount of the phospholipids; 1-palmitoyl-2-[16-(acryloyloxy)palmitoyl]-sn-glycero-3-phosphorylcholine or residues thereof are present in an amount from about 30 mole percent to about 50 mole percent of the total amount of the phospholipids; and 1,2-dipalmitoyl-sn-glycero-3-[phospho-rac-3-lysyl(1-glycerol))] (chloride salt) or residues thereof are present in an amount from about 2 mole percent to about 15 mole percent of the total amount of the phospholipids.

Figure 4:
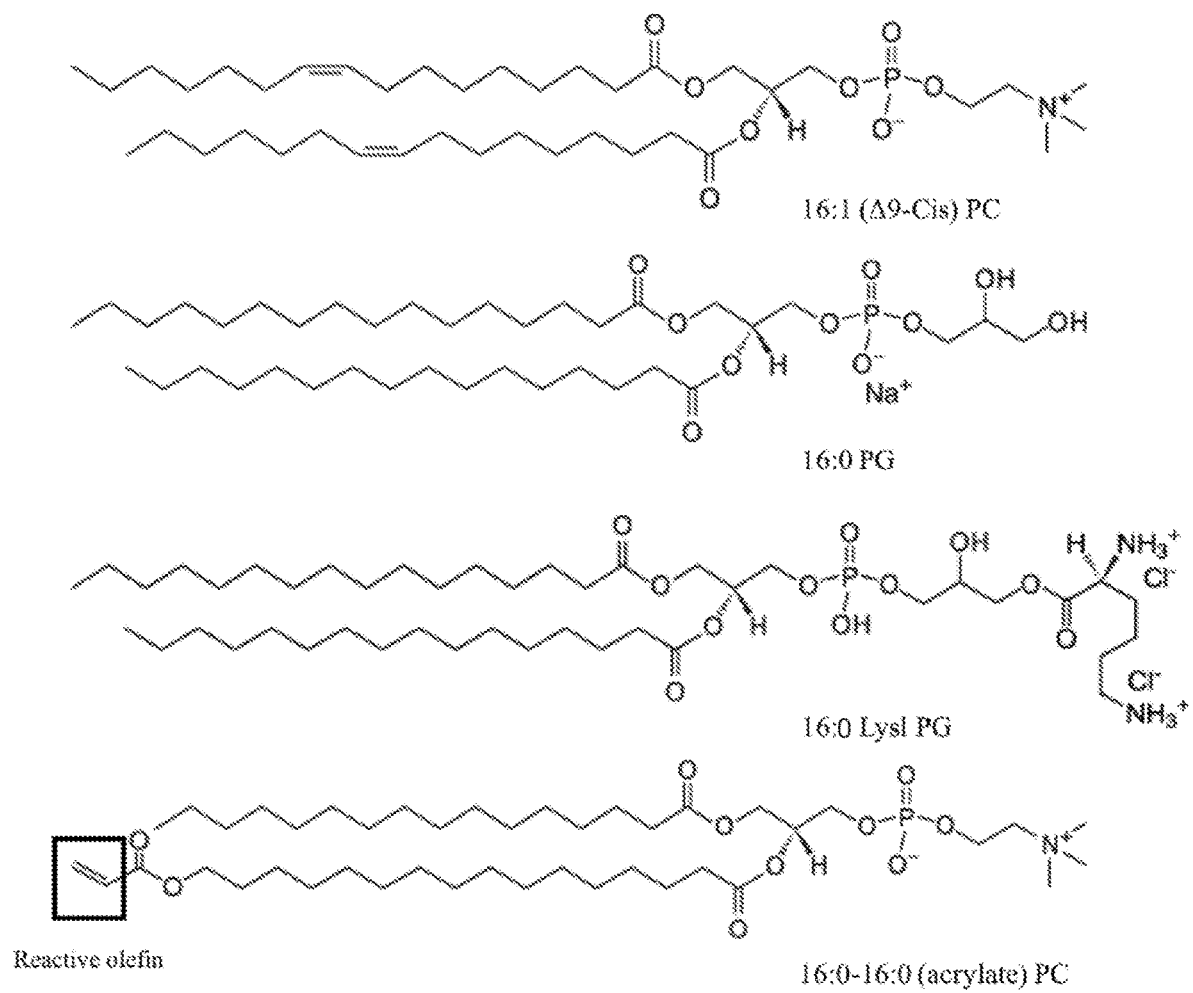
FIG. 4: Schematic of principle apparatus components (phospholipids) for "carrier" liposomal particle.

The organization and stability of the "carrier" particle apparatus is promoted by the crosslinking of 16:0 acrylate PC phospholipid tail groups, upon the formation of bilayers in an aqueous solution. The crosslinking of tail groups is driven by a photo-initiator (e.g. 2-Hydroxy-4'-(2-hydroxyethoxy)-2-methylpropiophenone [HEM]), which forms a radical intermediate at carbon-16 (FIG. 4; 16:0 acrylate PC, reactive terminal olefin) upon exposure to UV light. The radical intermediate reacts with other neighboring tail groups, containing a terminal olefin, in a chain reaction, until there are no more reactive terminal olefins. It should also be appreciated that the organization and stability of the "carrier" particle to encapsulate the sub-chamber liposome nanoparticle is promoted by enhancements in the charge character of the 16:0 lysl PG phospholipid head group. During the formation of the "carrier" particle, negatively charged moieties (e.g., phosphate groups) in sub-chamber liposome nanoparticles are drawn to the "carrier" bilayers-containing positively charged 16:0 lysl PG head groups. As the "carrier" bilayers associate, sub-chamber liposome nanoparticles are trapped, or encapsulated, in the newly formed "carrier" liposome. As a result, the "carrier" particle promotes high-encapsulation efficiencies (>60%) of sub-chamber liposome nanoparticles through a positive ion-based gradient.

Figure 5:
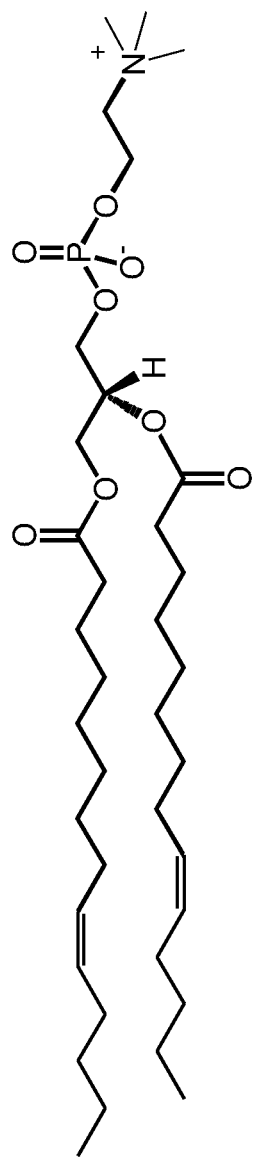
FIG. 5: Schematic representation of phospholipid head and tail group interactions.
Figure 5:
Figure 5:
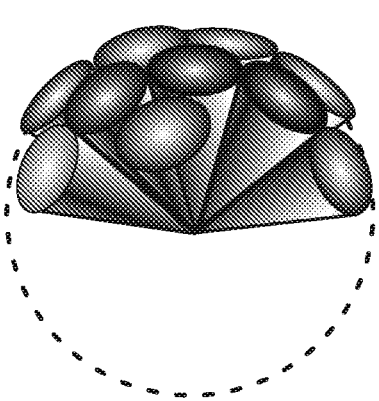
Figure 6:
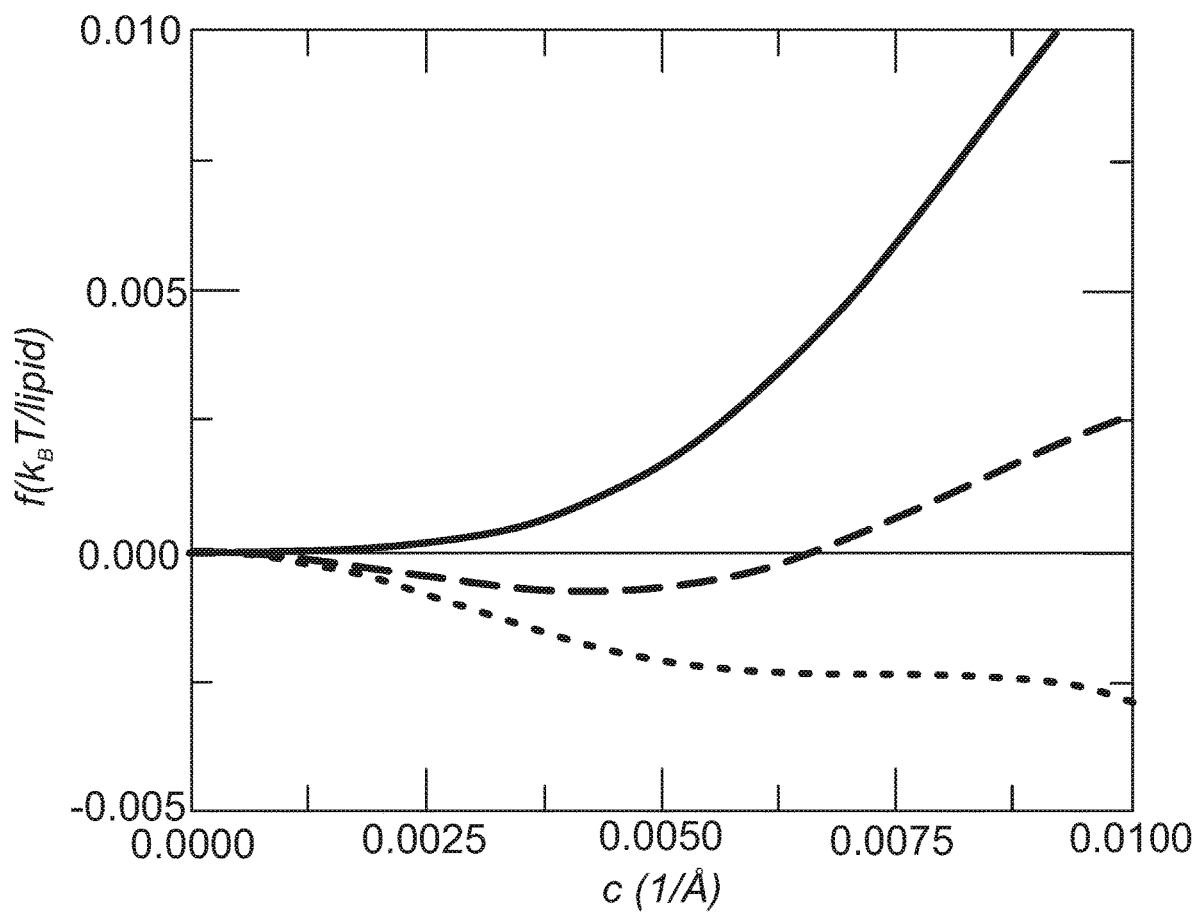
FIG. 6: Modeling of phospholipid bilayers with and without PEG. Minimum free energy as a function of curvature for a lipid/PEG-lipid bilayer containing 9.15% (solid line), 9.5% (dashed line), and 9.7% (dotted line) of PEG-lipid.[5]

The structural organization of the "carrier" and sub-chamber liposome nanoparticle's phospholipids are relevant to certain embodiments of the invention. In particular, the length of the tail group drives the curvature, and therefore, diameter of the liposomal nanoparticle. Phospholipids-containing shorter carbon-length tail groups are susceptible to forming shorter angles with other similar phospholipids (FIG. 5). As the non-polar tail groups become shorter, the curvature of the bilayer is driven by the opposing forces of the head group.[3] Another key aspect of the structural organization is the permeability of the "carrier" particle, which is driven by the cis-, or trans-, confirmation of the unsaturated phospholipids. From Gillespe et al. and first principles, these parameters control the release rate of sub-chamber liposome nanoparticles from the "carrier" particle.[4] Another key aspect of the structural organization is the covalent addition of water-soluble poly (ethylene glycol) (PEG) to the surface of the "carrier" and/or sub-chamber particles. As shown in FIG. 6, the curvature of a PEG-functionalized bilayer is energetically stable compared to bilayers, not functionalized with PEG.[5]

In should also be appreciated that carrier liposomes particles 12 of FIG. 1 without the sub-chamber liposome particles 14 are also useful for delivering payloads. In this variation, a carrier liposome composition is provided. The carrier liposome composition includes a plurality of carrier liposomes particles. Each carrier liposomes particle includes a carrier phospholipid bilayer comprising carrier phospholipids and having an average diameter less than 1 micron. In particular, it is noted the carrier liposome particle has a diameter of 150 to 170 nm (e.g., average diameter for a plurality of particles or individual particle diameter). As set forth above, the carrier liposome particles include conjugated tail group covalent linkages. Characteristically, the carrier phospholipid bilayer includes 1,2-dipalmitoleoyl-sn-glycero-3-phosphocholine; 1,2-dipalmitoyl-sn-glycero-3-phospho-(1'-rac-glycerol)(sodium salt); 1-palmitoyl-2-[16-(acryloyloxy)palmitoyl]-sn-glycero-3-phosphorylcholine; and 1,2-dipalmitoyl-sn-glycero-3-[phospho-rac-(3-lysyl(1-glycerol))] (chloride salt). Advantageously, the carrier liposome particles can include therapeutic/diagnostic payload encapsulated by the carrier liposome particle. Examples of therapeutic/diagnostic payloads includes, but are not limited to, molecule drugs, polynucleotides, macromolecular proteins, and combinations thereof. In a refinement, the therapeutic/diagnostic payload is selected from the group consisting of fluorescent proteins, cytokines, antibodies, and combinations thereof. It should be appreciated that all the properties of carrier liposomes particles 12 set forth above are also applicable in this variation except those related to sub-chamber liposome particles.

In another embodiment, a method for forming the multi-vesicular liposome composition set forth above is provided. The method includes a step of forming a plurality of sub-chamber liposome nanoparticles where the plurality of sub-chamber liposome nanoparticles have an average nanoparticle diameter less than about 50 nm. The plurality of sub-chamber liposome nanoparticles are formed from a sub-chamber liposome-forming composition that includes a first payload. A plurality of carrier liposome particles having an average particle diameter less than about 1 micron is then formed. The plurality of carrier liposome particles is formed from a carrier liposome-forming composition (e.g., the phospholipids are combined typically in a solvent), that includes the plurality of sub-chamber liposome nanoparticles such that sub-chamber liposome nanoparticles are encapsulated (i.e., contained within) by carrier liposome particles. In one variation, the sub-chamber liposome-forming composition includes 1,2-dimyristoleoyl-sn-glycero-3-phosphocholine; 1,2-dimyristoyl-sn-glycero-3-phospho-(1'-rac-glycerol) (sodium salt), 1-palmitoyl-2-[16-(acryloyloxy) palmitoyl]-sn-glycero-3-phosphorylcholine, and 1,2-dipalmitoyl-sn-glycero-3-phosphoethanolamine-N-[methoxy(polyethylene glycol)-350] (ammonium salt) which are mixed together typically in a solvent. A first payload is optionally combined with the sub-chamber liposome-forming composition and then crosslinked which actinic radiation (e.g., UV light)

Similarly, in this variation, the carrier liposome-forming composition can include 1,2-dipalmitoleoyl-sn-glycero-3-phosphocholine; 1,2-dipalmitoyl-sn-glycero-3-phospho-(1'-rac-glycerol) (sodium salt); 1-palmitoyl-2-[16-(acryloyloxy) palmitoyl]-sn-glycero-3-phosphorylcholine, and; 1,2-dipalmitoyl-sn-glycero-3-[phospho-rac-(3-lysyl(1-glycerol))](chloride salt) which are mixed together typically in a solvent. A second payload is optionally combined with the sub-chamber liposome-forming composition and then crosslinked with actinic radiation (e.g., UV light)

It should also be appreciated as set forth above, the carrier liposome-forming composition includes a second payload that is different from the sub-chamber liposome nanoparticles. In a refinement, the carrier liposome-forming composition includes one or more additional payloads that are different from the sub-chamber liposome nanoparticles. Details of the first and second payloads are set forth above.

Figure 7A:
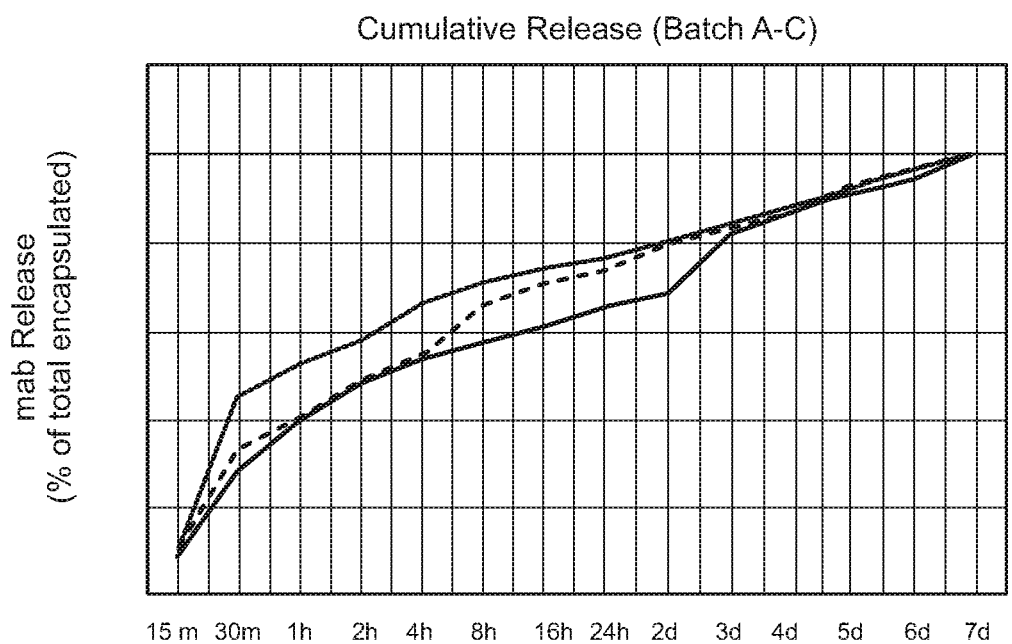
FIGS. 7A and 7B: Release of monoclonal antibody from CLSTER invention. (A) Cumulative release of monoclonal antibody from CLSTER for three iterations, measured over 7 days. (B) Mean of the three iterations of monoclonal antibody cumulative release, measured over 7 days.
Figure 7B:
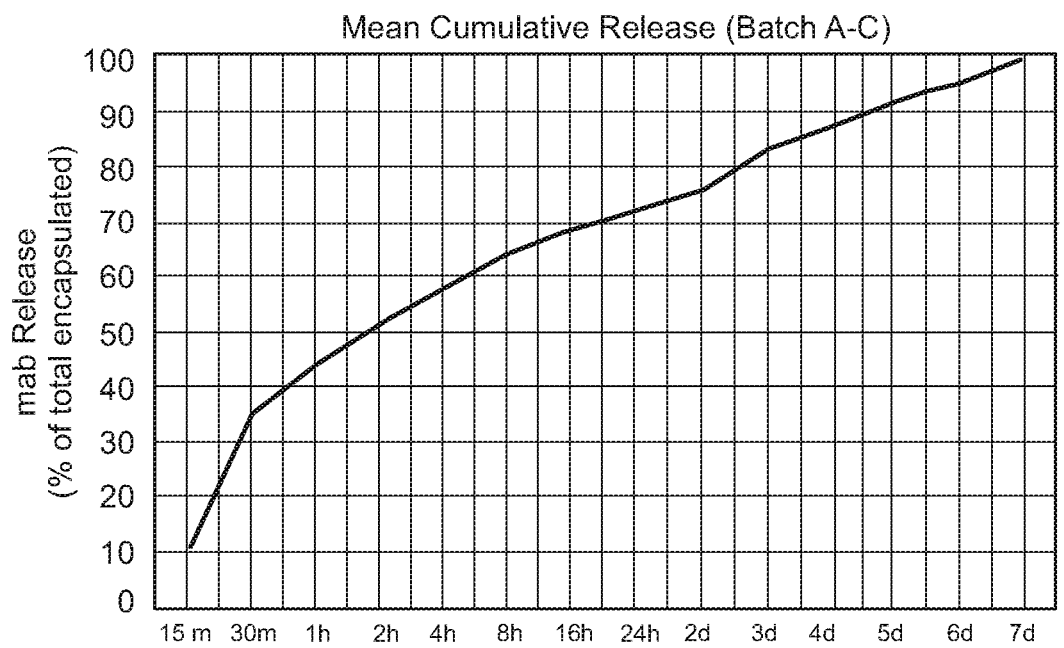
Figure 8A:
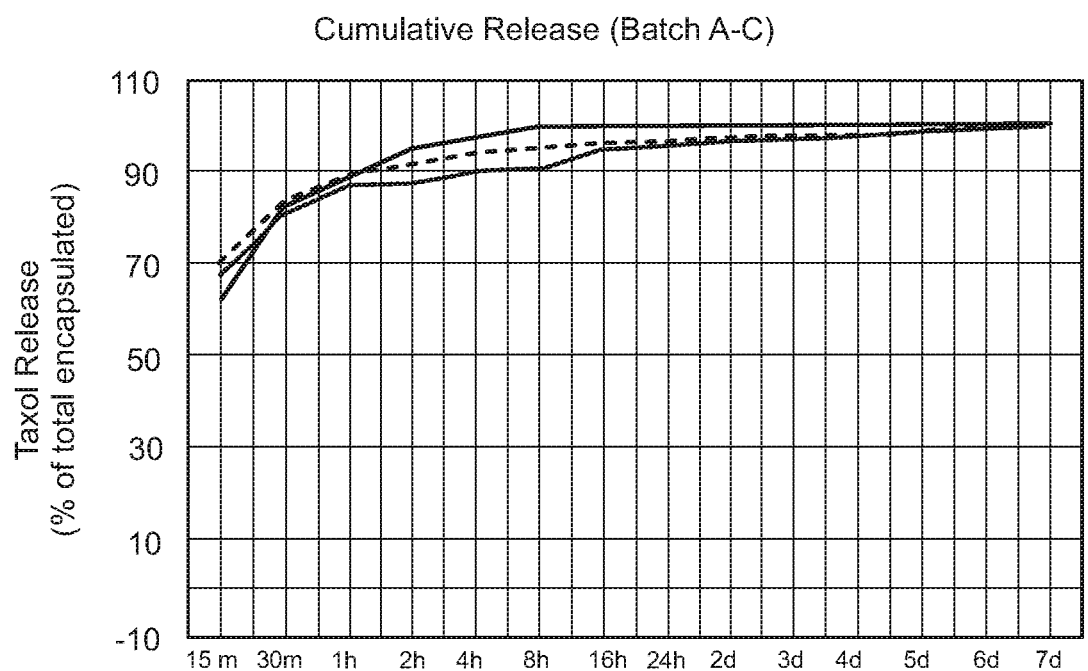
FIGS. 8A and 8B: Release of Taxol from CLSTER invention. (A) Cumulative release of Taxol from CLSTER for three iterations, measured over 7 days. (B) Mean of the three iterations of Taxol cumulative release, measured over 7 days.
Figure 8B:
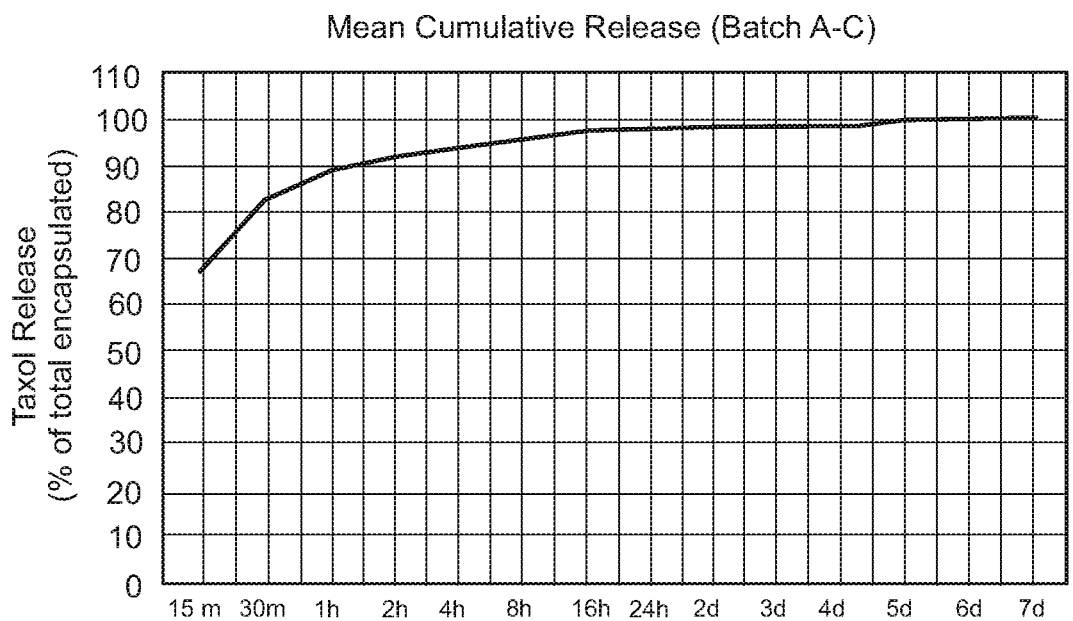

In a variation, the sub-chamber liposome nanoparticle, or apparatus, can encapsulate therapeutically relevant biomolecules, formulated for sustained (7 days) release. In one aspect, the sub-chamber liposome nanoparticle apparatus is capable of encapsulating therapeutically relevant polypeptides, which fold to form proteins (e.g., monoclonal antibodies [mAb]), at efficiencies greater than 79%. Once the mAb-encapsulated sub-chamber liposome nanoparticle apparatuses are packaged in "carrier" particles, or apparatuses, the fraction released of mAb is measured over the course of 7 days (FIG. 7A) for three iterations. Based on the mean cumulative release of batches A-C, the invention takes up to 7 days to release 99.9% of its payload (FIG. 7B). In another aspect, the sub-chamber liposome nanoparticle apparatus is capable of encapsulating therapeutically relevant small molecules (e.g., Taxol) at efficiencies greater than 10%. Encapsulation efficiency is defined as the percentage of the payload molecule that actually is encapsulated during the manufacturing process. For example, if one starts with 10 ng of dox and 1 ng was encapsulated (with the remaining 9 ng being washed out during manufacture), 10% encapsulation efficiency is achieved. Once the Taxol-encapsulated sub-chamber liposome nanoparticle apparatuses are packaged in "carrier" apparatuses, the fraction released of Taxol is measured over the course of 7 days (FIG. 8A) for three iterations. Based on the mean cumulative release of batches A-C, the invention takes up to 4 days to release 99.9% of its payload (FIG. 8B).

The following examples illustrate the various embodiments of the present invention. Those skilled in the art will recognize many variations that are within the spirit of the present invention and scope of the claims.

Methods

Solutions:

The following solutions may be made and stored ahead of time 1. 100 mM Bis-Tris-Propane
    a. Prepare a 100 mM solution by dissolving 1.412 g of Bis-Tris Propane in 50 mL water.
    b. Pass the solution through a 0.45 μm vacuum filter.
    c. Autoclave the solution.
    d. For DLS analysis, filter through a 0.02 μm filter.
2. 1× Phosphate Buffer Solution (1×PBS)
    a. Prepare a 1× solution by dissolving one tablet in 100 mL water.
    b. Pass the solution through a 0.45 μm vacuum filter.
    c. Autoclave the solution.
    d. For DLS analysis, filter through a 0.02 μm filter.
3. 2% Sucrose Cryoprotectant Solution
    a. Prepare a 2% solution by dissolving 1 g of Sucrose in 50 mL 1×PBS
    b. For DLS analysis, filter through a 0.02 μm filter.
    c. Store at −80°.

The following solutions should be made immediately prior to use and kept in a dark container 4. 20% (wt) TEMED
    a. Add 130 μL of TEMED to 370 μL of 100 mM Bis-Tris-Propane.
    b. Mix thoroughly and keep away from light.
5. 2% (wt) HEM
    a. Weigh 20 mg of HEM and dissolve in 1 mL of Methanol.
    b. Mix thoroughly and keep away from light.

Procedure:

20 nm Liposome Formulation

6. To a borosilicate glass tube, add the following volumes from the set stocks:
    a. 4.24 μL of 14:1-(Δ9-cis)-PC Lipid
    b. 6.42 μL of 14:0 PEG-350 PE Lipid
    c. 10.86 μL of 14:0 PG Lipid
    d. 25.40 μL of 16:0-16:0 Acrylate PC Lipid
    e. Hydrophobic payload to be encapsulated, if any.

TABLE 2

Formulation table used to calculate the volumes from the lipid stocks.

|  | 14:1-(Δ9-cis)-PC | 16:0 PEG-350 PE | 14:0 PG | 16:0-16:0 Acrylate PC |
|---|---|---|---|---|
| Molar Ratio | 0.4 | 0.2 | 10 | 1.0 |
| Total = 0.410 μmol | 0.0629 | 0.0315 | 0.158 | 0.1581 |
| MW (g/mol) | 673.901 | 1019.287 | 688.845 | 804.086 |
| Total (initial) = X ug | 42.4 | 32.1 | 108.6 | 127.0 |
| Concentration (μg/L) | 10 | 5 | 10 | 5 |
| Volume (μL) | 4.24 | 6.42 | 10.86 | 25.40 |

7. Vortex lipids for 10 mins at 1 minute intervals.
8. Blow a stream of compressed air across the top of the borosilicate tube in order to create a vortex. Continue until the solvent is fully evaporated.
9. Remove remaining chloroform by applying vacuum for 30 minutes in a desiccation chamber. (At this point, begin preparation of lipid bilayer for Carrier Nanoparticle, steps 26-29).

10. Resuspend lipids in 100 μL of 100 mM Bis-Tris propane solution. Vortex for one minute for every 10 minutes for 1 hour.

11. Transfer lipid solution to either chilled microcentrifuge tube or 15 mL conical vial.

12. Incubate solution at 4° C. for 5 minutes.

13. Sonicate the lipid solution at setting 4, for 30 one second pulses.

14. Add any hydrophilic small molecule drug, therapeutic antibody, or DNA/RNA sample to be loaded, at concentration consistent with target drug loading.

15. Incubate lipid solution at 37° C. on orbital shaker for 1 hour.

16. Cool solution at 4° for 15 minutes.

17. Heat shock the lipid solution at 42° for 20 seconds.

18. Cool solution at 4° for 10 minutes.

19. During this step, begin resuspension of lipid bi-layer for the Carrier Nanoparticle, step 27.

20. Heat shock the lipid solution at 42° for 20 seconds.

21. Cool solution at 4° for 10 minutes.

22. Vortex solution vigorously for one minute.

23. Add 2.5 μL of 2% wt HEM (Methanol) and 2.5 μL of 20% wt TEMED (aq.) to lipid solution.

24. Treat lipid solution under a UV lamp (370 nm) for 90 seconds.

25. Vortex solution vigorously for one minute.

26. Spin lipid solution at 14 k rpm for 15 minutes.

27. Remove supernatant and add to Carrier Nanoparticle solution.

150 nm Carrier Liposome

28. To a borosilicate glass tube, add the following volumes from the set stocks:

TABLE 3

Formulation table used to calculate the volumes from the lipid stocks.

| | 16:1-(Δ9-cis)-PC | 16:0 PG | 16:0-16:0 Acrylate PC | 16:0 Lysyl PG |
|---|---|---|---|---|
| Molar Ratio | 0.5 | 0.3 | 1.0 | 0.2 |
| Total = 1.545 μmol | 0.378 | 0.252 | 0.789 | 0.126 |
| MW (g/mol) | 730.007 | 744.952 | 804.086 | 924.064 |
| Total (initial) = X μg | 276.0 | 187.6 | 634.5 | 116.4 |
| Concentration (g/L) | 25 | 10 | 5 | 1 |
| Volume (μL) | 11.04 | 8.68 | 126.9 | 116.4 |

29. Vortex lipids for 10 mins at 1 minute intervals.

30. Blow a stream of compressed air across the top of the borosilicate tube in order to create a vortex. Continue until the solvent is fully evaporated.

31. Remove remaining chloroform by applying vacuum for 30 minutes in a desiccation chamber.

32. Resuspend lipids in 100 μL of 100 mM Bis-Tris propane solution. Vortex for one minute for every 10 minutes for 1 hour.

33. Transfer lipid solution to either chilled microcentrifuge tube.

34. Incubate solution at 4° C. for 5 minutes.

35. Sonicate the lipid solution at setting 4, for 10 one second pulses.

36. Add the small particle solution (made in steps 1-25), along with any hydrophilic small molecule drug, therapeutic antibody, or DNA/RNA sample to be loaded, at concentration consistent with target drug loading.

37. Incubate lipid solution at 37° C. on orbital shaker for 1 hour.

38. Cool solution at 4 for 15 minutes.

39. Heat shock the lipid solution at 42° for 20 seconds.

40. Cool solution at 4° for 10 minutes.

41. Heat shock the lipid solution at 42° for 20 seconds.

42. Cool solution at 4° for 10 minutes.

43. Add 10 μL of 2% wt HEM (in Acetone or MeOH) and 10 μL of 20% wt TEMED (aq.) to lipid solution.

44. Treat lipid solution under a UV lamp (370 nm) for 90 seconds.

45. Spin lipid solution at 14 k rpm for 60 minutes.

46. Remove supernatant and resuspend in 400 μL of 1×PBS.

47. Spin lipid solution at 14 k rpm for 5 minutes.

48. Remove supernatant and resuspend in 100 μL of 1×PBS or cryoprotectant solution.

49. Determine concentration of the liposome particle solution, and lyophilize or use immediately, as appropriate.

Results

Figure 9A:
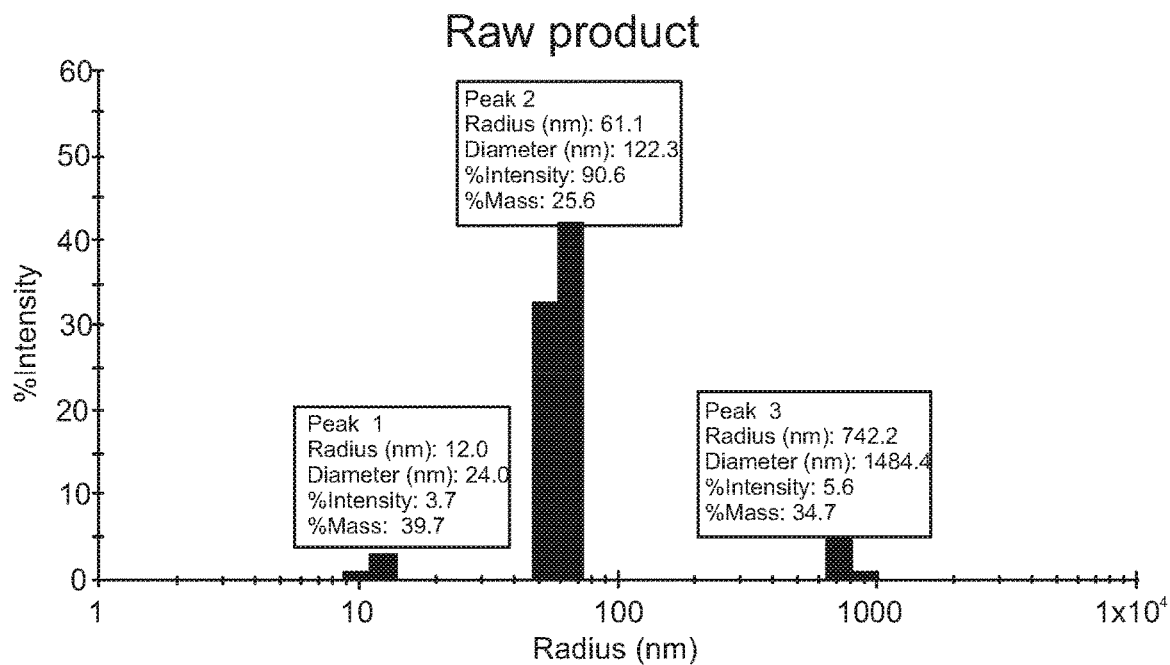
FIG. 9A: Hydrodynamic radius of the raw product.
Figure 9B:
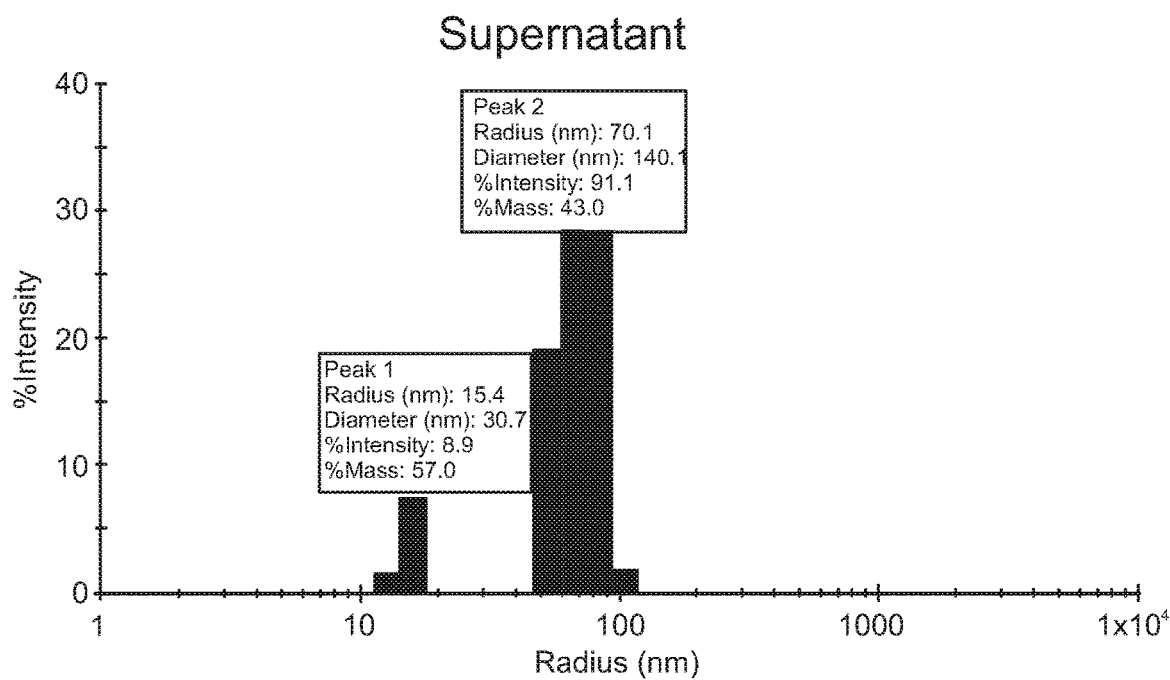
FIG. 9B is hydrodynamic radius of product that was not pulled down in centrifugation (i.e., left in the supernatant).
Figure 9C:
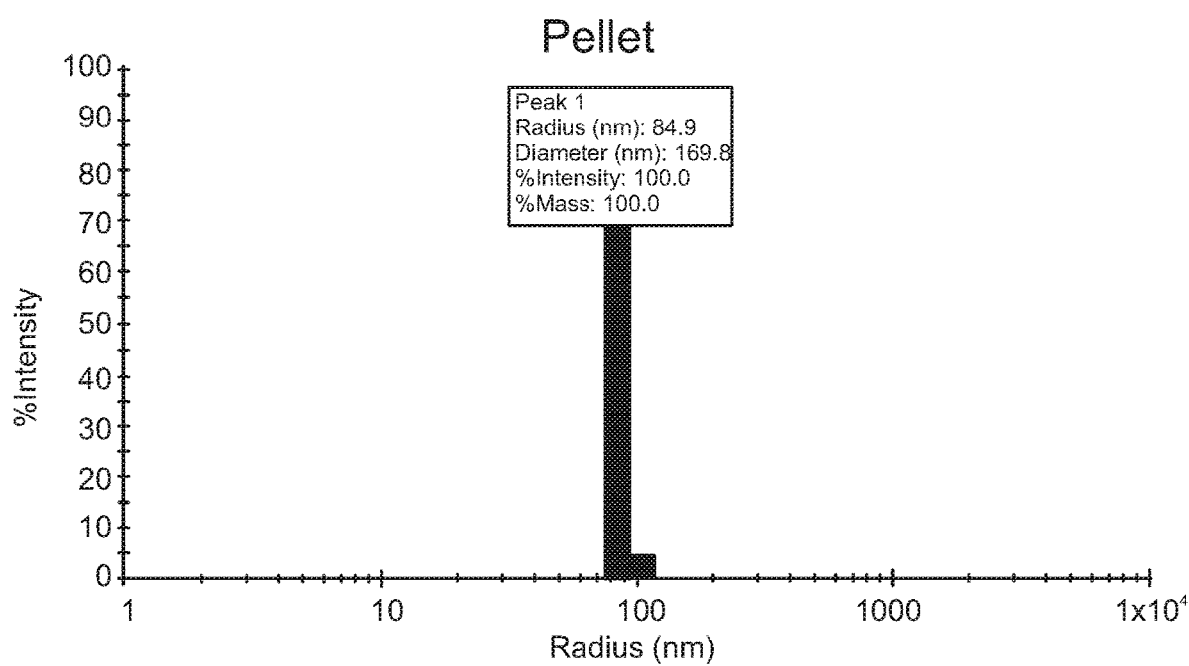

FIGS. 9A, 9B, and 9C provide plots of hydrodynamic diameter for CLSTER[DNA], CLSTER[Dox], and CLSTER[BSA] nanoparticles. CLSTER manufacturing protocol produces CLSTER nanoparticles with a hydrodynamic diameter of 170 nm and low polydispersity. The standard CLSTER manufacturing protocol was used to make a batch of CLSTER nanoparticles containing plasmid DNA. The hydrodynamic size and polydispersity of the manufactured CLSTER nanoparticles were quantified by dynamic light scattering (DLS) using a Wyatt Technology DynaPro Plate Reader 3. In FIG. 9A, analysis of the raw product (i.e., the manufactured CLSTER nanoparticles prior to filtration, washing, and centrifugation) revealed a strong signal indicating that the CLSTER nanoparticles had a mean hydrodynamic diameter of 122.3 nm. The peak with the smaller hydrodynamic diameter (24.0 nm) is most likely to be unencapsulated sub-chamber nanoparticles. The peak with the larger hydrodynamic diameter (1484.4 nm) is most likely to be leftover lipid bilayer that was not dispersed during sonication. With reference to FIG. 9B, after filtration with a 0.45 um syringe filter and centrifugation at 14,000 g, the supernatant was analyzed by DLS. The unencapsulated sub-chamber nanoparticles remained in the supernatant (peak with hydrodynamic diameter of 30.7 nm), as did CLSTER nanoparticles with a hydrodynamic diameter on the lower end of the expected size range (140.1 nm). With reference to FIG. 9C, the pellet resulting from centrifugation at 14,000 g was resuspended in phosphate-buffered saline and analyzed by DLS. The narrow peak indicates a homogenous population of CLSTER nanoparticles with low polydispersity and a mean hydrodynamic radius of 169.8 nm.

FIGS. 10A, 10B, and 10C provide visualizations of CLSTER nanoparticles and released sub-chamber nanoparticles by transmission electron microscopy. The standard CLSTER manufacturing protocol was used to make a batch of CLSTER nanoparticles containing plasmid DNA. The CLSTER nanoparticles were stored for three days at 4° C. in phosphate-buffered saline, then prepared for analysis by transmission electron microscopy. The carrier nanoparticles (large circles) can be visualized containing sub-chamber nanoparticles (small circles). In addition, sub-chamber nanoparticles that have been released during the three-day incubation can also be visualized (arrowheads point to examples).

FIGS. 1A and 1/B provide analysis of mCherry mRNA expression in human breast cancer cells that have been treated with CLSTR[mCherry] nanoparticles. CLSTER nanoparticles deliver plasmid DNA to human cells in vitro, and phospholipid tail crosslinking is essential for this process. The standard CLSTER manufacturing protocol was used to make a batch of CLSTER nanoparticles encapsulating a plasmid encoding mCherry red fluorescent protein driven by a ubiquitous promoter (CAG). Human breast cancer cells (MDA-MB-231) were grown to 80% confluence in 24 well plates using standard cell culture techniques, then serum-starved for 24 hours. The cells were then treated with sufficient CLSTR[mCherry] nanoparticles to deliver 250 ng of plasmid DNA. Control wells were treated with one of the conditions listed in the table. In all cases, treatment media was removed after five hours and replaced with complete cell culture medium. The cells were cultured for a further 48 hours, then complete RNA harvested from cells in each treatment condition and analyzed for expression of mCherry mRNA by reverse-transcription PCR. Cells transfected with CLSTER[mCherry] showed strong expression of mCherry mRNA at the expected amplicon size of 346 bp (lane 7). This was comparable to mCherry expression elicited by treatment with a standard transfection agent (GenJet™ In Vitro DNA Transfection Reagent, SignaGen Laboratories, lanes 5 and 6) delivering the same amount of plasmid DNA (250 ng). No mCherry mRNA was detected in cells left untreated, or that were treated with 250 ng plasmid DNA alone or with GenJet transfection agent alone (lanes 2, 3, and 4, respectively). Strikingly, no mCherry mRNA expression was elicited using a batch of CLSTER[mCherry] manufactured using the standard protocol but skipping the UV exposure step, thus eliminating crosslinking of phospholipid tails in the lipid bilayers (lane 8). This suggests that the enhanced stability of the CLSTER lipid bilayers conferred by this crosslinking is essential to maintenance of the CLSTER nanoparticles' structure for long enough to be taken up by cells in vitro.

FIGS. 12A, 12B, and 12C are plots of the release kinetics for CLSTER[DNA], CLSTER[Dox], and CLSTER[BSA] nanoparticles. CLSTER nanoparticles demonstrate long-term payload retention and steady release kinetics. The standard CLSTER manufacturing protocol was used to make batches of CLSTER nanoparticles containing plasmid DNA, doxorubicin, or protein (bovine serum albumin, BSA). The CLSTER nanoparticles were shaken at 250 rpm at 37° C. for one week. At the timepoints indicated, the CLSTER nanoparticle were centrifuged at 14,000 g at 4° C., the supernatant removed and retained for quantitation of released payload, and the CLSTER nanoparticles resuspended in fresh phosphate buffered saline (PBS). Aliquots of each supernatant were mixed with a 10× volume of hexane, and incubated for fifteen minutes at room temperature to remove lipids. Samples of the aqueous layer (containing hydrophilic payload) were analyzed by UV/Vis spectrophotometry and the amount of payload in each quantitated. In the cases of all payloads tested, the CLSTER nanoparticles exhibited an initial burst release of the payload followed by a steady release of the payload over seven days. In all cases, a significant percentage of the loaded payload remained encapsulated within the CLSTER nanoparticles after seven days. (A) CLSTER[DNA] nanopartices released 35% of their payload within the first hour of incubation. A further 45% of the payload was steadily released over the remaining incubation period, with 20% payload retention after the full 7 day incubation period. (B) CLSTER[Dox] nanoparticles released 30% of their payload within the first hour of incubation. A further 45% of the payload was steadily released over the remaining incubation period, with 15% payload retention after the full 7 day incubation period. (C) CLSTER[BSA] nanoparticles released 73% of their payload within the first hour of incubation. A further 23.5% of the payload was steadily released over the remaining incubation period, with 3.5% payload retention after the full 7 day incubation period.

FIG. 13 is a bar chart showing encapsulation efficiency of payloads in CLSTER[DNA], CLSTER[Dox], and CLSTER[BSA] nanoparticles. The standard CLSTER manufacturing protocol was used to make batches of CLSTER nanoparticles containing plasmid DNA, doxorubicin, or protein (bovine serum albumin, BSA). Aliquots of each batch of CLSTER nanoparticles were mixed with a 10× volume of hexane, and incubated for fifteen minutes at room temperature to remove lipids. Samples of the aqueous layer (containing hydrophilic payload) were analyzed by UV/Vis spectrophotometry and the amount of payload in each quantitated. The percentage encapsulation efficiency for each payload was calculated by dividing the total amount of payload encapsulated within each batch divided by the total amount of payload used during manufacture, multiplied by 100%.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

Sankaram, Mantripagada B., and Sinil Kim. Preparation of Multivesicular Liposomes for Controlled Release of Active Agents. Mantripragada B. Sankaram, assignee. Patent CA2199004 C. 13 Sep. 1994.

Kim, Sinil, and Stephen B. Howell. Multivesicular liposomes with controlled release of active agents encapsulated in the presence of a hydrochloride. Sinil Kim, assignee. U.S. Pat. No. 6,071,534 A. 15 Feb. 1988.

Rovira-Bru, M., Thompson, D. H., Szleifer, 1. "Size and Structure of Spontaneously Forming Liposomes in Lipid/PEG-Lipid Mixtures." *Biophysical Journal.* 2002. 83(5); 2419-2439.

Gillespie D T. Exact stochastic simulation of coupled chemical reactions. J Phys Chem. 1977; 81(25):2340-2361. doi:10.1021/j100540a008.

Alberts B, Johnson A, Lewis J, et al. Molecular Biology of the Cell. 4th edition. New York: Garland Science; 2002. The Lipid Bilayer.Available from: https://www.ncbi.nlm.nih.gov/books/NBK26871/.

What is claimed is:

1. A multivesicular liposome composition including a plurality of multivesicular liposomes, each multivesicular liposome comprising:
    a carrier liposome particle including a carrier phospholipid bilayer comprising carrier phospholipids and having an average diameter less than 1 micron; and
    at least one sub-chamber liposome nanoparticle including a sub-chamber phospholipid bilayer comprising sub-chamber phospholipids and having an average diameter less than about 50 nm, the carrier liposome particle encapsulating the at least one sub-chamber liposome nanoparticle, wherein tail groups of the carrier phospholipids are larger on average than the tail groups of the sub-chamber phospholipids, wherein the carrier liposome particles includes crosslinks between phospholipids in the same layer of the carrier phospholipid bilayer and crosslinks between different layers of the carrier phospholipid bilayer and wherein at least one sub-chamber liposome nanoparticle includes crosslinks between phospholipids in the same layer of the sub-chamber phospholipid bilayer and crosslinks between different layers of the sub-chamber phospholipid bilayer.

2. The multivesicular liposome composition of claim 1 wherein the sub-chamber liposome nanoparticle has a diameter from 20 to 50 nm.

3. The multivesicular liposome composition of claim 2 wherein the carrier liposome particle has a diameter of 150 to 170 nm.

4. The multivesicular liposome composition of claim 1 wherein the carrier liposome particle and the sub-chamber liposome nanoparticle each independently include conjugated tail group covalent linkages.

5. The multivesicular liposome composition of claim 1 wherein the sub-chamber phospholipid bilayer includes 1,2-dimyristoleoyl-sn-glycero-3-phosphocholine; 1,2-dimyristoyl-sn-glycero-3-phospho-(1'-rac-glycerol) (sodium salt), 1-palmitoyl-2-[16-(acryloyloxy)palmitoyl]-sn-glycero-3-phosphorylcholine; and 1,2-dipalmitoyl-sn-glycero-3-phosphoethanolamine-N-[methoxy(polyethylene glycol)-350] (ammonium salt).

6. The multivesicular liposome composition of claim 1 wherein the carrier phospholipid bilayer includes 1,2-dipalmitoleoyl-sn-glycero-3-phosphocholine; 1,2-dipalmitoyl-sn-glycero-3-phospho-(1'-rac-glycerol) (sodium salt); 1-palmitoyl-2-[16-(acryloyloxy)palmitoyl]-sn-glycero-3-phosphorylcholine; and 1,2-dipalmitoyl-sn-glycero-3-[phospho-rac-(3-lysyl(1-glycerol))] (chloride salt).

7. The multivesicular liposome composition of claim 1 further comprising a therapeutic/diagnostic payload encapsulated by the at least one sub-chamber liposome nanoparticle and/or the carrier liposome particle.

8. The multivesicular liposome composition of claim 7 wherein the therapeutic/diagnostic payload is selected from the group consisting of molecule drugs, polynucleotides, macromolecular proteins, and combinations thereof.

9. The multivesicular liposome composition of claim 7 wherein the therapeutic/diagnostic payload is selected from the group consisting of fluorescent proteins, cytokines, antibodies, and combinations thereof.

10. The multivesicular liposome composition of claim 1 wherein the multivesicular liposome composition includes a plurality of carrier liposome particles and a plurality of sub-chamber liposome nanoparticles such that different subsets of the plurality of carrier liposome particles and/or subsets of the plurality of sub-chamber liposome nanoparticles include different payloads.

11. The multivesicular liposome composition of claim 1 wherein reversible linkages attach sub-chamber liposome nanoparticles to an inner surface of the carrier liposome particle.

12. A method of forming a multivesicular liposome composition including a plurality of multivesicular liposomes, each multivesicular liposome comprising:
a carrier liposome particle including a carrier phospholipid bilayer comprising carrier phospholipids and having an average diameter less than 1 micron; and
at least one sub-chamber liposome nanoparticle including a sub-chamber phospholipid bilayer comprising sub-chamber phospholipids and having an average diameter less than about 50 nm, the carrier liposome particle encapsulating the at least one sub-chamber liposome nanoparticle, wherein tail groups of the carrier phospholipids are larger on average than the tail groups of the sub-chamber phospholipids, the method comprising:
a) forming a plurality of sub-chamber liposome nanoparticles, the plurality of sub-chamber liposome nanoparticles having an average nanoparticle diameter less than about 50 nm, the plurality of sub-chamber liposome nanoparticles being formed from a sub-chamber liposome-forming composition that includes a first payload; and
b) forming a plurality of carrier liposome particles having an average nanoparticle diameter less than about 1 micron, the plurality of carrier liposome particles being formed from a carrier liposome-forming composition that includes the plurality of sub-chamber liposome nanoparticles such that sub-chamber liposome nanoparticles are encapsulated by carrier liposome particles.

13. The method of claim 12 wherein the sub-chamber liposome-forming composition includes 1,2-dimyristoleoyl-sn-glycero-3-phosphocholine; 1,2-dimyristoyl-sn-glycero-3-phospho-(1'-rac-glycerol) (sodium salt), 1-palmitoyl-2-[16-(acryloyloxy)palmitoyl]-sn-glycero-3-phosphorylcholine; and 1,2-dipalmitoyl-sn-glycero-3-phosphoethanolamine-N-[methoxy(polyethylene glycol)-350] (ammonium salt).

14. The method of claim 12 wherein the carrier liposome-forming composition includes 1,2-dipalmitoleoyl-sn-glycero-3-phosphocholine; 1,2-dipalmitoyl-sn-glycero-3-phospho-(1'-rac-glycerol) (sodium salt); 1-palmitoyl-2-[16-(acryloyloxy)palmitoyl]-sn-glycero-3-phosphorylcholine; and 1,2-dipalmitoyl-sn-glycero-3-[phospho-rac-(3-lysyl(1-glycerol))] (chloride salt).

15. The method of claim 12 wherein the carrier liposome-forming composition includes a second payload.

16. The method of claim 15 wherein the carrier liposome-forming composition includes one or more additional payloads.

17. The method of claim 15 wherein the first payload and the second payload each independently include a therapeutic/diagnostic agent.

18. The method of claim 17 wherein the therapeutic/diagnostic agent is selected from the group consisting of molecule drugs, polynucleotides, macromolecular proteins, and combinations thereof.

19. A carrier liposome composition including a plurality of carrier liposomes particles, each carrier liposomes particle comprising:
a carrier phospholipid bilayer comprising carrier phospholipids and having an average diameter less than 1 micron.

20. The carrier liposome composition of claim 19 wherein the carrier liposome particles have an average diameter of 150 to 170 nm.

21. The carrier liposome composition of claim 19 wherein the carrier liposome particles include conjugated tail group covalent linkages.

22. The carrier liposome composition of claim 19 wherein the carrier phospholipid bilayer includes 1,2-dipalmitoleoyl-sn-glycero-3-phosphocholine; 1,2-dipalmitoyl-sn-glycero-3-phospho-(1'-rac-glycerol) (sodium salt); 1-palmitoyl-2-[16-(acryloyloxy)palmitoyl]-sn-glycero-3-phosphorylcholine; and 1,2-dipalmitoyl-sn-glycero-3-[phospho-rac-(3-lysyl(1-glycerol))] (chloride salt).

23. The carrier liposome composition of claim 19 further comprising a therapeutic/diagnostic payload encapsulated by the carrier liposome particles.

24. The carrier liposome composition of claim 23 wherein the therapeutic/diagnostic payload is selected from the group consisting of molecule drugs, polynucleotides, macromolecular proteins, and combinations thereof.

25. The carrier liposome composition of claim 23 wherein the therapeutic/diagnostic payload is selected from the group consisting of fluorescent proteins, cytokines, antibodies, and combinations thereof.

26. The carrier liposome composition of claim 1 wherein the sub-chamber liposome nanoparticle's phospholipid bilayers are locked in segments that migrate along the surface of a multivesicular liposome.

* * * * *